US007087234B1

(12) United States Patent
Scott et al.

(10) Patent No.: US 7,087,234 B1
(45) Date of Patent: Aug. 8, 2006

(54) RECOMBINANT MULTIVALENT VIRAL VACCINE

(75) Inventors: Fred W. Scott, Brooktondale, NY (US); Christopher K. Ngichabe, Kikuyu (KE); Liangbiao Hu, Baltimore, MD (US); Joseph J. Esposito, Atlanta, GA (US)

(73) Assignees: Cornell Research Foundation, Inc., Ithaca, NY (US); The United States of America as represented by the Department of Health and Human Services, Washington, DC (US)

( * ) Notice: Subject to any disclaimer, the term of this patent is extended or adjusted under 35 U.S.C. 154(b) by 577 days.

(21) Appl. No.: 09/873,881

(22) Filed: Jun. 4, 2001

Related U.S. Application Data

(63) Continuation of application No. 08/552,369, filed on Nov. 3, 1995, now Pat. No. 6,241,989, which is a continuation-in-part of application No. 08/190,789, filed on Jan. 27, 1994, now abandoned, which is a continuation of application No. 07/726,609, filed on Jul. 9, 1991, now abandoned.

(51) Int. Cl.
*A61K 39/12* (2006.01)

(52) U.S. Cl. .............................. 424/199.1; 424/201.1; 424/202.1; 424/221.1; 424/232.1; 435/69.1; 435/69.3; 435/235.1; 435/252.3; 435/320.1

(58) Field of Classification Search ............. 424/199.1, 424/201.1, 202.1, 221.1, 232.1; 435/235.1, 435/320.1, 69.1, 69.3, 252.3
See application file for complete search history.

(56) References Cited

U.S. PATENT DOCUMENTS

| 4,971,793 | A |   | 11/1990 | Wood et al. |           |
|-----------|---|---|---------|-------------|-----------|
| 5,266,313 | A |   | 11/1993 | Esposito et al. |       |
| 5,656,275 | A |   | 8/1997  | Wasmoen et al. |        |
| 5,770,211 | A | * | 6/1998  | Wasmoen et al. | 424/199.1 |
| 5,820,869 | A |   | 10/1998 | Wasmoen et al. |        |
| 5,849,303 | A |   | 12/1998 | Wasmoen et al. |        |
| 6,241,989 | B1| * | 6/2001  | Scott et al. | 424/199.1 |

OTHER PUBLICATIONS

Hu et al., "Construction and Characterization of Raccoonpoxvirus (RCNV) Recombinant Expressing Feline Panleukopenia virus -vp2 (FPV), Rabies-G (RAB), and Feline Calicivirus (FCV) Capsid Proteins"; Abstract for ASV Meeting of Jul. 9-13, 1994.

Lodmell, et al., Raccoon Poxvirus Recombinants Expressing the Rabies Virus Nucleoprotein Protect Mice Against Lethal Rabies Virus Infection, Journal of Virology, Jun. 1991, pp. 3400-3405.

Parrish, et al., Canine Host Range and a Specific Epitope Map Along with Variant Sequences in the Capsid Protein Gene of Canine Parvovirus and Related Feline, Mink, and Raccoon Parvoviruses, Journal of Virology, 1988, 166:293-307.

Parrish, et al., Mapping Specific Functions in the Capsid Structure of Canine Parvovirus and Feline Panleukophenia Virus Using Infectious Plasmid Clones, Journal of Virology, 1991, 183:195-205.

Martyn, et al., Nucleotide Sequence of Feline Panleukopenia Virus: Comparison With Canine Parvovirus Identifies Host-Specific Differences, Journal of General Virology, 1990, 71:2747-2753.

Carlson, et al., Cloning and Sequence of DNA Encoding Structural Proteins of the Autonomous Parvovirus Feline Panleukopenia Virus, Journal of Virology, Sep. 1985, pp. 574-582.

Esposito, et al., Successful Oral Rabies Vaccination of Reccoons With Raccoon Poxvirus Recombinants Expressing Rabies Virus Glycoprotein, Journal of Virology, 1988, 165:313-316.

Vennema, et al., Primary Structure of the Membrane and Nucleocapsid Protein Genes of Feline Infectious Peritonitis Virus and Immunogenicity of Recombinant Vaccinia Viruses in Kittens, Journal of Virology, 1991, 181:327-335.

Falkner, et al., *Escherichia coli* gpt Gene Provides Dominant Selection for Vaccinia Virus Open Reading Frame Expression Vectors, Journal of Virology, Jun. 1988, vol. 62, No. 6, pp. 1849-1854.

* cited by examiner

*Primary Examiner*—Ulrike Winkler
(74) *Attorney, Agent, or Firm*—Hodgson Russ LLP

(57) ABSTRACT

The present invention relates to multivalent recombinant raccoon poxviruses, containing more than one exogenous gene inserted into either the thymidine kinase gene, the hemagglutinin gene, or a combination thereof. Disclosed is the use of the multivalent recombinant raccoon poxviruses as vaccines to immunize felines against subsequent challenge by feline pathogens. Also disclosed is a method of making a multivalent recombinant raccoon poxvirus by a recombination process involving the construction of an insertion vector into which the exogenous genes are inserted, and flanking the inserted genes are sequences which can recombine into the raccoon poxvirus thymidine kinase gene, or the hemagglutinin gene, or a combination thereof; introducing both the insertion vector containing the exogenous genes, and raccoon poxvirus into susceptible host cells; and selecting the recombinant raccoon poxvirus from the resultant plaques.

10 Claims, 7 Drawing Sheets

FIG. 6B

SEQUENCE LISTING

<160> NUMBER OF SEQ ID NOS: 19

<210> SEQ ID NO 1
<211> LENGTH: 2254
<212> TYPE: DNA
<213> ORGANISM: feline panleukopenia virus
<220> FEATURE:
<223> OTHER INFORMATION:

<400> SEQUENCE: 1

```
atg agt gat gga gca gtt caa cca gac ggt ggt caa cct gct gtc          45
Met Ser Asp Gly Ala Val Gln Pro Asp Gly Gly Gln Pro Ala Val
1               5                   10                  15 aga aat gaa aga gct aca gga tct ggg aac ggg tct gga ggc ggg          90
Arg Asn Glu Arg Ala Thr Gly Ser Gly Asn Gly Ser Gly Gly Gly
            20                  25                  30 ggt ggt ggt ggt tct ggg ggt gtg ggg att tct acg ggt act ttc         135
Gly Gly Gly Gly Ser Gly Gly Val Gly Ile Ser Thr Gly Thr Phe
        35                  40                  45 aat aat cag acg gaa ttt aaa ttt ttg gaa aac gga tgg gtg gaa         180
Asn Asn Gln Thr Glu Phe Lys Phe Leu Glu Asn Gly Trp Val Glu
    50                  55                  60 atc aca gca aac tca agc aga ctt gta cat tta aat atg cca gaa         225
Ile Thr Ala Asn Ser Ser Arg Leu Val His Leu Asn Met Pro Glu
65                  70                  75 agt gaa aat tat aaa aga gta gtt gta aat aat atg gat aaa act         270
Ser Glu Asn Tyr Lys Arg Val Val Val Asn Asn Met Asp Lys Thr
                80                  85                  90 gca gtt aaa gga aac atg gct tta gat gac act cat gta caa att         315
Ala Val Lys Gly Asn Met Ala Leu Asp Asp Thr His Val Gln Ile
            95                  100                 105 gta aca cct tgg tca ttg gtt gat gca aat gct tgg gga gtt tgg         360
Val Thr Pro Trp Ser Leu Val Asp Ala Asn Ala Trp Gly Val Trp
        110                 115                 120 ttt aat cca gga gat tgg caa cta att gtt aat act atg agt gag         405
Phe Asn Pro Gly Asp Trp Gln Leu Ile Val Asn Thr Met Ser Glu
    125                 130                 135 ttg cat tta gtt agt ttt gaa caa gaa att ttt aat gtt gtt tta         450
Leu His Leu Val Ser Phe Glu Gln Glu Ile Phe Asn Val Val Leu
140                 145                 150 aag act gtt tca gaa tct gct act cag cca cca act aaa gtt tat         495
Lys Thr Val Ser Glu Ser Ala Thr Gln Pro Pro Thr Lys Val Tyr
                155                 160                 165 aat aat gat tta act gca tca ttg atg gtt gca tta gat agt aat         540
Asn Asn Asp Leu Thr Ala Ser Leu Met Val Ala Leu Asp Ser Asn
            170                 175                 180 aat act atg cca ttt act cca gca gct atg aga tct gag aca ttg         585
```

-continued

|   |   |
|---|---|
| Asn Thr Met Pro Phe Thr Pro Ala Ala Met Arg Ser Glu Thr Leu<br>                185                 190                 195 |   |
| ggt ttt tat cca tgg aaa cca acc ata cca act cca tgg aga tat<br>Gly Phe Tyr Pro Trp Lys Pro Thr Ile Pro Thr Pro Trp Arg Tyr<br>            200                 205                 210 | 630 |
| tat ttt caa tgg gat aga aca tta ata cca tct cat act gga act<br>Tyr Phe Gln Trp Asp Arg Thr Leu Ile Pro Ser His Thr Gly Thr<br>            215                 220                 225 | 675 |
| agt ggc aca cca aca aat ata tat cat ggt aca gat cca gat gat<br>Ser Gly Thr Pro Thr Asn Ile Tyr His Gly Thr Asp Pro Asp Asp<br>            230                 235                 240 | 720 |
| gtt caa ttt tat act att gaa aat tct gtg cca gta cac tta cta<br>Val Gln Phe Tyr Thr Ile Glu Asn Ser Val Pro Val His Leu Leu<br>            245                 250                 255 | 765 |
| aga aca ggt gat gaa ttt gct aca gga aca ttt ttt ttt gat tgt<br>Arg Thr Gly Asp Glu Phe Ala Thr Gly Thr Phe Phe Phe Asp Cys<br>            260                 265                 270 | 810 |
| aaa cca tgt aga cta aca cat aca tgg caa aca aac aga gca ttg<br>Lys Pro Cys Arg Leu Thr His Thr Trp Gln Thr Asn Arg Ala Leu<br>            275                 280                 285 | 855 |
| ggc tta cca cca ttt cta aat tct ttg cct caa tct gaa gga gct<br>Gly Leu Pro Pro Phe Leu Asn Ser Leu Pro Gln Ser Glu Gly Ala<br>            290                 295                 300 | 900 |
| act aac ttt ggt gat ata gga gtt caa caa gat aaa aga cgt ggt<br>Thr Asn Phe Gly Asp Ile Gly Val Gln Gln Asp Lys Arg Arg Gly<br>            305                 310                 315 | 945 |
| gta act caa atg gga aat aca gac tat att act gaa gct act att<br>Val Thr Gln Met Gly Asn Thr Asp Tyr Ile Thr Glu Ala Thr Ile<br>            320                 325                 330 | 990 |
| atg aga cca gct gag gtt ggt tat agt gca cca tat tat tct ttt<br>Met Arg Pro Ala Glu Val Gly Tyr Ser Ala Pro Tyr Tyr Ser Phe<br>            335                 340                 345 | 1035 |
| gaa gcg tct aca caa ggg cca ttt aaa ata cct att gca gca gga<br>Glu Ala Ser Thr Gln Gly Pro Phe Lys Ile Pro Ile Ala Ala Gly<br>            350                 355                 360 | 1080 |
| cgg ggg gga gcg caa aca gat gaa aat caa gca gca gat ggt gat<br>Arg Gly Gly Ala Gln Thr Asp Glu Asn Gln Ala Ala Asp Gly Asp<br>            365                 370                 375 | 1125 |
| cca aga tat gca ttt ggt aga caa cat ggt caa aaa act act aca<br>Pro Arg Tyr Ala Phe Gly Arg Gln His Gly Gln Lys Thr Thr Thr<br>            380                 385                 390 | 1170 |
| aca gga gaa aca cct gag aga ttt aca tat ata gca cat caa gat<br>Thr Gly Glu Thr Pro Glu Arg Phe Thr Tyr Ile Ala His Gln Asp<br>            395                 400                 405 | 1215 |
| aca gga aga tat cca gca gga gat tgg att caa aat att aac ttt<br>Thr Gly Arg Tyr Pro Ala Gly Asp Trp Ile Gln Asn Ile Asn Phe<br>            410                 415                 420 | 1260 |
| aac ctt cct gta aca aat gat aat gta ttg cta cca aca gat cca<br>Asn Leu Pro Val Thr Asn Asp Asn Val Leu Leu Pro Thr Asp Pro<br>            425                 430                 435 | 1305 |
| att gga ggt aaa aca gga atc aac tat act aat ata ttt aat act<br>Ile Gly Gly Lys Thr Gly Ile Asn Tyr Thr Asn Ile Phe Asn Thr<br>            440                 445                 450 | 1350 |
| tat ggt cct tta act gca tta aat aat gta cca cca gtt tat cca<br>Tyr Gly Pro Leu Thr Ala Leu Asn Asn Val Pro Pro Val Tyr Pro<br>            455                 460                 465 | 1395 |
| aat ggt caa att tgg gat aaa gaa ttt gat act gac tta aaa cca<br>Asn Gly Gln Ile Trp Asp Lys Glu Phe Asp Thr Asp Leu Lys Pro<br>            470                 475                 480 | 1440 |

-continued

```
aga ctt cat gta aat gca cca ttt gtt tgt caa aat aat tgt cct       1485
Arg Leu His Val Asn Ala Pro Phe Val Cys Gln Asn Asn Cys Pro
            485                 490                 495 ggt caa tta ttt gta aaa gtt gcg cct aat tta aca aat gaa tat       1530
Gly Gln Leu Phe Val Lys Val Ala Pro Asn Leu Thr Asn Glu Tyr
            500                 505                 510 gat cct gat gca tct gct aat atg tca aga att gta act tac tca       1575
Asp Pro Asp Ala Ser Ala Asn Met Ser Arg Ile Val Thr Tyr Ser
            515                 520                 525 gat ttt tgg tgg aaa ggt aaa tta gta ttt aaa gct aaa cta aga       1620
Asp Phe Trp Trp Lys Gly Lys Leu Val Phe Lys Ala Lys Leu Arg
            530                 535                 540 gca tct cat act tgg aat cca att caa caa atg agt att aat gta       1665
Ala Ser His Thr Trp Asn Pro Ile Gln Gln Met Ser Ile Asn Val
            545                 550                 555 gat aac caa ttt aac tat cta cca aat aat att gga gct atg aaa       1710
Asp Asn Gln Phe Asn Tyr Leu Pro Asn Asn Ile Gly Ala Met Lys
            560                 565                 570 att gta tat gaa aaa tct caa cta gca cct aga aaa tta tat           1752
Ile Val Tyr Glu Lys Ser Gln Leu Ala Pro Arg Lys Leu Tyr
            575                 580 taatatactt actatgtttt tatggttatt acatatcaac tagcacctag            1802
aaaattatat taatatactt actatgtttt tatgtttatt acatattatt            1852
ttaagattaa ttaaattaca acatagaaat attgtacttg tatttgatat            1902
aggatttaga aggtttgtta tatggtatac aataactgta agaaatagaa            1952
gaacatttag atcatggtta gtatggtata caataactgt aagaaataga            2002
agaacattta gatcatggtt agtagttttgt tttataaaat gtaattgtaa           2052
actattaatg tatgttgtta tggtgtgggt ggttggttgg tttgccctta            2102
gaatatgtta aggaccaaaa aaatcaataa aagacattta aaacttaatg            2152
gtctcgtata ctgtctataa ggtgaactaa ccttaccata agtatcaact            2202
tgtctttaag ggggggggtgg gtgggagatg cacaatatca gtagactgac           2252
tg                                                                 2254
```

<210> SEQ ID NO 2
<211> LENGTH: 1575
<212> TYPE: DNA
<213> ORGANISM: rabies virus
<220> FEATURE:
<223> OTHER INFORMATION:

<400> SEQUENCE: 2

```
atg gtt cct cag gct ctc ctg ttt gta ccc ctt ctg gtt ttt            42
Met Val Pro Gln Ala Leu Leu Phe Val Pro Leu Leu Val Phe
  1               5                  10 cca ttg tgt ttt ggg aaa ttc cct att tac acg ata cta gac             84
Pro Leu Cys Phe Gly Lys Phe Pro Ile Tyr Thr Ile Leu Asp
 15                  20                  25 aag ctt ggt ccc tgg agc ccg att gac ata cat cac ctc agc            126
Lys Leu Gly Pro Trp Ser Pro Ile Asp Ile His His Leu Ser
         30                  35                  40 tgc cca aac aat ttg gta gtg gag gac gaa gga tgc acc aac            168
Cys Pro Asn Asn Leu Val Val Glu Asp Glu Gly Cys Thr Asn
             45                  50                  55 ctg tca ggg ttc tcc tac atg gaa ctt aaa gtt gga tac atc            210
Leu Ser Gly Phe Ser Tyr Met Glu Leu Lys Val Gly Tyr Ile
             60                  65                  70
```

-continued

| | |
|---|---|
| tta gcc ata aaa atg aac ggg ttc act tgc aca ggc gtt gtg<br>Leu Ala Ile Lys Met Asn Gly Phe Thr Cys Thr Gly Val Val<br>              75                     80 | 252 |
| acg gag gct gaa acc tac act aac ttc gtt ggt tat gtc aca<br>Thr Glu Ala Glu Thr Tyr Thr Asn Phe Val Gly Tyr Val Thr<br>85               90                    95 | 294 |
| acc acg ttc aaa aga aag cat ttc cgc cca aca cca gat gca<br>Thr Thr Phe Lys Arg Lys His Phe Arg Pro Thr Pro Asp Ala<br>       100                 105                 110 | 336 |
| tgt aga gcc gcg tac aac tgg aag atg gcc ggt gac ccc aga<br>Cys Arg Ala Ala Tyr Asn Trp Lys Met Ala Gly Asp Pro Arg<br>           115                 120               125 | 378 |
| tat gaa gag tct cta cac aat ccg tac cct gac tac cgc tgg<br>Tyr Glu Glu Ser Leu His Asn Pro Tyr Pro Asp Tyr Arg Trp<br>              130               135              140 | 420 |
| ctt cga act gta aaa acc acc aag gag tct ctc gtt atc ata<br>Leu Arg Thr Val Lys Thr Thr Lys Glu Ser Leu Val Ile Ile<br>                  145                 150 | 462 |
| tct cca agt gta gca gat ttg gac cca tat gac aga tcc ctt<br>Ser Pro Ser Val Ala Asp Leu Asp Pro Tyr Asp Arg Ser Leu<br>155                  160                 165 | 504 |
| cac tcg agg gtc ttc cct agc ggg aag tgc tca gga gta gcg<br>His Ser Arg Val Phe Pro Ser Gly Lys Cys Ser Gly Val Ala<br>       170                 175                 180 | 546 |
| gtg tct tct acc tac tgc tcc act aac cac gat tac acc att<br>Val Ser Ser Thr Tyr Cys Ser Thr Asn His Asp Tyr Thr Ile<br>              185               190              195 | 588 |
| tgg atg ccc gag aat ccg aga cta ggg atg tct tgt gac att<br>Trp Met Pro Glu Asn Pro Arg Leu Gly Met Ser Cys Asp Ile<br>           200                 205              210 | 630 |
| ttt acc aat agt aga ggg aag aga gca tcc aaa ggg agt gag<br>Phe Thr Asn Ser Arg Gly Lys Arg Ala Ser Lys Gly Ser Glu<br>                  215                 220 | 672 |
| act tgc ggc ttt gta gat gaa aga ggc cta tat aag tct tta<br>Thr Cys Gly Phe Val Asp Glu Arg Gly Leu Tyr Lys Ser Leu<br>225                  230                 235 | 714 |
| aaa gga gca tgc aaa ctc aag tta tgt gga gtt cta gga ctt<br>Lys Gly Ala Cys Lys Leu Lys Leu Cys Gly Val Leu Gly Leu<br>       240                 245                 250 | 756 |
| aga ctt atg gat gga aca tgg gtc gcg atg caa aca tca aat<br>Arg Leu Met Asp Gly Thr Trp Val Ala Met Gln Thr Ser Asn<br>              255               260              265 | 798 |
| gaa acc aaa tgg tgc gct ccc gat cag ttg gtg aac ctg cac<br>Glu Thr Lys Trp Cys Ala Pro Asp Gln Leu Val Asn Leu His<br>                  270               275              280 | 840 |
| gac ttt cgc tca gac gaa att gag cac ctt gtt gta gag gag<br>Asp Phe Arg Ser Asp Glu Ile Glu His Leu Val Val Glu Glu<br>                     285                 290 | 882 |
| ttg gtc agg aag aga gag gag tgt ctg gat gca cta gag tcc<br>Leu Val Arg Lys Arg Glu Glu Cys Leu Asp Ala Leu Glu Ser<br>295                  300                 305 | 924 |
| atc atg aca aac aag tca gtg agt ttc aga cgt ctc agt cat<br>Ile Met Thr Asn Lys Ser Val Ser Phe Arg Arg Leu Ser His<br>       310                 315                 320 | 966 |
| tta aga aaa ctt gtc cct ggg ttt gga aaa gca tat acc ata<br>Leu Arg Lys Leu Val Pro Gly Phe Gly Lys Ala Tyr Thr Ile<br>                  325                 330              335 | 1008 |
| ttc aac aag acc ttg atg gaa gcc gat gct cac tac aag tca<br>Phe Asn Lys Thr Leu Met Glu Ala Asp Ala His Tyr Lys Ser | 1050 |

```
                340             345             350
gtc aga act tgg aat gag atc ctc cct tca aaa ggg tgt tta           1092
Val Arg Thr Trp Asn Glu Ile Leu Pro Ser Lys Gly Cys Leu
                355                     360 aga gtt ggg ggg agg tgt cat cct cat gtg aac ggg gtg ttt           1134
Arg Val Gly Gly Arg Cys His Pro His Val Asn Gly Val Phe
365             370                     375 ttc aat ggt ata ata tta gga cct gac ggc aat gtc tta atc           1176
Phe Asn Gly Ile Ile Leu Gly Pro Asp Gly Asn Val Leu Ile
    380                 385                     390 cca gag atg caa tca tcc ctc ctc cag caa cat atg gag ttg           1218
Pro Glu Met Gln Ser Ser Leu Leu Gln Gln His Met Glu Leu
        395                 400                 405 ttg gaa tcc tcg gtt atc ccc ctt gtg cac ccc ctg gca gac           1260
Leu Glu Ser Ser Val Ile Pro Leu Val His Pro Leu Ala Asp
            410                 415                 420 ccg tct acc gtt ttc aag gac ggt gac gag gct gag gat ttt           1302
Pro Ser Thr Val Phe Lys Asp Gly Asp Glu Ala Glu Asp Phe
                425                 430 gtt gaa gtt cac ctt ccc gat gtg cac aat cag gtc tca gga           1344
Val Glu Val His Leu Pro Asp Val His Asn Gln Val Ser Gly
435             440                     445 gtt gac ttg ggt ctc ccg aac tgg ggg aag tat gta tta ctg           1386
Val Asp Leu Gly Leu Pro Asn Trp Gly Lys Tyr Val Leu Leu
    450                 455                     460 agt gca ggg gcc ctg act gcc ttg atg ttg ata att ttc ctg           1428
Ser Ala Gly Ala Leu Thr Ala Leu Met Leu Ile Ile Phe Leu
        465                 470                 475 atg aca tgt tgt aga aga gtc aat cga tca gaa cct acg caa           1470
Met Thr Cys Cys Arg Arg Val Asn Arg Ser Glu Pro Thr Gln
            480                 485                 490 cac aat ctc aga ggg aca ggg agg gag gtg tca gtc act ccc           1512
His Asn Leu Arg Gly Thr Gly Arg Glu Val Ser Val Thr Pro
                495                 500 caa agc ggg aag atc ata tct tca tgg gaa tca cac aag agt           1554
Gln Ser Gly Lys Ile Ile Ser Ser Trp Glu Ser His Lys Ser
505             510                     515 ggg ggt gag acc aga ctg tga                                       1575
Gly Gly Glu Thr Arg Leu
    520

<210> SEQ ID NO 3
<211> LENGTH: 44
<212> TYPE: DNA
<213> ORGANISM: P11 late promoter and leader sequence
<220> FEATURE:
<223> OTHER INFORMATION:

<400> SEQUENCE: 3
taaaaatata gtagaatttc attttgtttt tttctatgct ataa              44

<210> SEQ ID NO 4
<211> LENGTH: 28
<212> TYPE: DNA
<213> ORGANISM: artificial sequence
<220> FEATURE:
<223> OTHER INFORMATION: forward primer

<400> SEQUENCE: 4
cgggatccat ttttccttcg tttgccat                                28
```

-continued

```
<210> SEQ ID NO 5
<211> LENGTH: 28
<212> TYPE: DNA
<213> ORGANISM: artificial sequence
<220> FEATURE:
<223> OTHER INFORMATION: reverse primer

<400> SEQUENCE: 5
cgggtaccga tttctccgtg ataggtat                                        28

<210> SEQ ID NO 6
<211> LENGTH: 18
<212> TYPE: DNA
<213> ORGANISM: artificial sequence
<220> FEATURE:
<223> OTHER INFORMATION: sequencing primer

<400> SEQUENCE: 6
ctacttgcat agataggt                                                   18

<210> SEQ ID NO 7
<211> LENGTH: 2007
<212> TYPE: DNA
<213> ORGANISM: feline calicivirus
<220> FEATURE:
<223> OTHER INFORMATION:

<400> SEQUENCE: 7 atg tgc tca acc tgc gct aac gtg ctt aaa tac tat gat tgg gat           45
Met Cys Ser Thr Cys Ala Asn Val Leu Lys Tyr Tyr Asp Trp Asp
  1               5                  10                  15 cct cac atc aaa ttg gta atc aac ccc aac aaa ttt cta cat gtt           90
Pro His Ile Lys Leu Val Ile Asn Pro Asn Lys Phe Leu His Val
                 20                  25                  30 ggc ttc tgc gat aac cct tta atg tgt tgt tat cct gaa tta cta1         135
Gly Phe Cys Asp Asn Pro Leu Met Cys Cys Tyr Pro Glu Leu Leu
                 35                  40                  45 cct gaa ttt ggc acc atg tgg gat tgt gat caa tcg cca ctc caa          180
Pro Glu Phe Gly Thr Met Trp Asp Cys Asp Gln Ser Pro Leu Gln
                 50                  55                  60 gtc tac ctt gag tca atc ctg ggt gat gat gaa tgg tcc tcc act          225
Val Tyr Leu Glu Ser Ile Leu Gly Asp Asp Glu Trp Ser Ser Thr
                 65                  70                  75 cat gaa gca att gac cca gtt gtg cca cca atg cat tgg gat gaa          270
His Glu Ala Ile Asp Pro Val Val Pro Pro Met His Trp Asp Glu
                 80                  85                  90 gcc gga aaa atc ttc caa cca cac cct ggc gtc ctt atg cat cac          315
Ala Gly Lys Ile Phe Gln Pro His Pro Gly Val Leu Met His His
                 95                 100                 105 ctc atc tgt aag gtt gca gaa gga tgg gac cca aac ctg cca ctt          360
Leu Ile Cys Lys Val Ala Glu Gly Trp Asp Pro Asn Leu Pro Leu
                110                 115                 120 ttc cgc ttg gaa gcg gac gat ggt tcc atc acg aca cct gaa cag          405
Phe Arg Leu Glu Ala Asp Asp Gly Ser Ile Thr Thr Pro Glu Gln
                125                 130                 135 gga aca atg gtt ggt gga gtc att gct gag ccc aac gcc caa atg          450
Gly Thr Met Val Gly Gly Val Ile Ala Glu Pro Asn Ala Gln Met
                140                 145                 150 tca acc gca gct gac atg gcc act ggg aaa agt gtg gac tct gag          495
Ser Thr Ala Ala Asp Met Ala Thr Gly Lys Ser Val Asp Ser Glu
                155                 160                 165 tgg gaa gcc ttc ttc tcc ttt cac act agt gtg aac tgg agc aca          540
Trp Glu Ala Phe Phe Ser Phe His Thr Ser Val Asn Trp Ser Thr
```

```
                170                 175                 180
tct gaa act cag ggg aag ata ctc ttt aaa caa tcc tta gga cca        585
Ser Glu Thr Gln Gly Lys Ile Leu Phe Lys Gln Ser Leu Gly Pro
                185                 190                 195 ttg ctc aac ccc tac ctt acc cat ctt gca aag ctg tat gtt gct        630
Leu Leu Asn Pro Tyr Leu Thr His Leu Ala Lys Leu Tyr Val Ala
                200                 205                 210 tgg tct ggt tct gtt gat gtt agg ttt tct att tct gga tct ggt        675
Trp Ser Gly Ser Val Asp Val Arg Phe Ser Ile Ser Gly Ser Gly
                215                 220                 225 gtc ttt gga ggg aaa tta gct gct att gtt gtg ccg cca gga att        720
Val Phe Gly Gly Lys Leu Ala Ala Ile Val Val Pro Pro Gly Ile
                230                 235                 240 gat cct gtt caa agt act tca atg ctg caa tat cct cat gtc ctc        765
Asp Pro Val Gln Ser Thr Ser Met Leu Gln Tyr Pro His Val Leu
                245                 250                 255 ttt gat gct cgt caa gtt gaa cct gtt atc ttt tcc att ccc gat        810
Phe Asp Ala Arg Gln Val Glu Pro Val Ile Phe Ser Ile Pro Asp
                260                 265                 270 cta aga agc acc tta tat cac ctt atg tct gac act gat acc aca        855
Leu Arg Ser Thr Leu Tyr His Leu Met Ser Asp Thr Asp Thr Thr
                275                 280                 285 tcg ttg gta atc atg gtg tac aat gat ctt att aac ccc tat gct        900
Ser Leu Val Ile Met Val Tyr Asn Asp Leu Ile Asn Pro Tyr Ala
                290                 295                 300 aat gac tca aac tct tcg ggc tgc att gtc act gtg gaa act aaa        945
Asn Asp Ser Asn Ser Ser Gly Cys Ile Val Thr Val Glu Thr Lys
                305                 310                 315 ccg ggg cca gat ttc aag ttt cac ctc tta aaa cct cct ggg tct        990
Pro Gly Pro Asp Phe Lys Phe His Leu Leu Lys Pro Pro Gly Ser
                320                 325                 330 atg tta act cac gga tct atc cca tct gat cta atc cca aaa tca       1035
Met Leu Thr His Gly Ser Ile Pro Ser Asp Leu Ile Pro Lys Ser
                335                 340                 345 tct tcg ctt tgg att gga aat cgg ttt tgg tct gac ata acc gat       1080
Ser Ser Leu Trp Ile Gly Asn Arg Phe Trp Ser Asp Ile Thr Asp
                350                 355                 360 ttt gta att cgg cct ttt gtg ttc cag gca aat cga cac ttt gat       1125
Phe Val Ile Arg Pro Phe Val Phe Gln Ala Asn Arg His Phe Asp
                365                 370                 375 ttc aac caa gag aca gca ggt tgg agc acc cca agg ttt cgc cca       1170
Phe Asn Gln Glu Thr Ala Gly Trp Ser Thr Pro Arg Phe Arg Pro
                380                 385                 390 att act atc act atc agt gtt aag gag tca gca aag ctt ggt att       1215
Ile Thr Ile Thr Ile Ser Val Lys Glu Ser Ala Lys Leu Gly Ile
                395                 400                 405 gga gtg gcc acc gac tac att gtt ccc ggc ata cca gat gga tgg       1260
Gly Val Ala Thr Asp Tyr Ile Val Pro Gly Ile Pro Asp Gly Trp
                410                 415                 420 ccc gac aca aca atc cca ggt gag ttg gta cct gtt ggt gac tat       1305
Pro Asp Thr Thr Ile Pro Gly Glu Leu Val Pro Val Gly Asp Tyr
                425                 430                 435 gcc atc act aat ggc acc aac aat gat atc acc aca gct gcg cag       1350
Ala Ile Thr Asn Gly Thr Asn Asn Asp Ile Thr Thr Ala Ala Gln
                440                 445                 450 tac gat gca gcc act gag att aga aac aac acc aat ttc aga ggc       1395
Tyr Asp Ala Ala Thr Glu Ile Arg Asn Asn Thr Asn Phe Arg Gly
                455                 460                 465 atg tac att tgt ggt tct ctt caa aga gct tgg ggg gat aag aag       1440
```

```
Met Tyr Ile Cys Gly Ser Leu Gln Arg Ala Trp Gly Asp Lys Lys
            470                 475                 480
att tca aat act gct ttt atc aca acc ggc acg gtt gat gga gcc    1485
Ile Ser Asn Thr Ala Phe Ile Thr Thr Gly Thr Val Asp Gly Ala
            485                 490                 495 aaa ttg ata ccc agt aat acc att gac caa aca aaa att gcc gta    1530
Lys Leu Ile Pro Ser Asn Thr Ile Asp Gln Thr Lys Ile Ala Val
            500                 505                 510 ttc caa gac aca cat gcg aat aag cat gtc cag acc tcg gac gac    1575
Phe Gln Asp Thr His Ala Asn Lys His Val Gln Thr Ser Asp Asp
            515                 520                 525 aca ttg gcc ctg ctt ggt tat act ggt att ggt gag gaa gca att    1620
Thr Leu Ala Leu Leu Gly Tyr Thr Gly Ile Gly Glu Glu Ala Ile
            530                 535                 540 ggt gct gac cgc gat aga gtt gtg cga att agc gtc ctc ccg gaa    1665
Gly Ala Asp Arg Asp Arg Val Val Arg Ile Ser Val Leu Pro Glu
            545                 550                 555 cgt ggc gca cgt ggt ggc aat cac cca atc ttc cac aaa aac tct    1710
Arg Gly Ala Arg Gly Gly Asn His Pro Ile Phe His Lys Asn Ser
            560                 565                 570 atc aag ctt ggt tat gta att agg tcc att gat gtg ttc aat tct    1755
Ile Lys Leu Gly Tyr Val Ile Arg Ser Ile Asp Val Phe Asn Ser
            575                 580                 585 caa att ctg cat acc tct agg caa ctt tcc ctc aat cat tac tta    1800
Gln Ile Leu His Thr Ser Arg Gln Leu Ser Leu Asn His Tyr Leu
            590                 595                 600 ttg tcg cct gac tcc ttt gct gtc tat agg att att gac tct aat    1845
Leu Ser Pro Asp Ser Phe Ala Val Tyr Arg Ile Ile Asp Ser Asn
            605                 610                 615 gga tcc tgg ttt gac ata ggc att gat aat gat gga ttt tct ttt    1890
Gly Ser Trp Phe Asp Ile Gly Ile Asp Asn Asp Gly Phe Ser Phe
            620                 625                 630 gtt ggt gta tca agt att ggt aaa tta gag ttt cct tta act gcc    1935
Val Gly Val Ser Ser Ile Gly Lys Leu Glu Phe Pro Leu Thr Ala
            635                 640                 645 tcc tac atg gga att caa ttg gca aaa att cga ctt gcc tct aac    1980
Ser Tyr Met Gly Ile Gln Leu Ala Lys Ile Arg Leu Ala Ser Asn
            650                 655                 660 att agg agt gtg atg aca aaa tta tga                            2007
Ile Arg Ser Val Met Thr Lys Leu
            665

<210> SEQ ID NO 8
<211> LENGTH: 582
<212> TYPE: DNA
<213> ORGANISM: artificial sequence
<220> FEATURE:
<223> OTHER INFORMATION: hemagglutinin left arm

<400> SEQUENCE: 8
attaaacgca aatatccatg gaaaacgcgc agtatacaga cgattttta              50 cagtatttgg agagttttat aggaagtata tagagtagaa ccagaatttt            100
gtaaaaataa atcacatttt tatactaata tgaaacaact atcgatagtt            150
atattgctac tatcgatagt atatacaacc aaacctcatc ctacacagat            200
atcaaaaaaa ctaggcgatg atgctactct atcgtgtaat agaaacaata            250
cacatggata tccttgtcatg agttcttggt ataagaaacc agactccatt           300
attctcttag cagccaaaaa cgatgtcgta tactttgatg attatacagc            350
```

```
ggataaagta tcatacgatt caccgtatga tactctagct acaattatta              400
caattaaatc attgacatct gcagatgcag gtacttatat atgcgcattc              450
tttataacat caacaaatga tacggataaa atagattatg aagaatactt              500
catagatttg gttgtaaatc cagctaatgt atccactatt gacgcgattc              550
tatcaggatc taatttctcc gtgataggta tc                                 582

<210> SEQ ID NO 9
<211> LENGTH: 447
<212> TYPE: DNA
<213> ORGANISM: artificial sequence
<220> FEATURE:
<223> OTHER INFORMATION: hemagglutinin right arm

<400> SEQUENCE: 9
ctctagcgcc taaccccagg cgaccgacga caacctttat gatacatata               50
atgaaccaat atctgtatca tcctcgatac caacaacggt agaaagtgtt              100
acaatatcta ctacaaaata tacaactagt gactttatag agatatttgg              150
cattgtttca ctaattttat tattggccgt ggcgattttc tgtattatat              200
tatttctgta gtggacggtc tcgtaaacaa gaaacaaata tattatagat              250
tttaactcag ataaatgtct ggaataatta aatctatcgt tttgagcgga              300
ccatctggtt ccggcaagac agctatagtc aggagactct tacaagatta              350
tggaaatata tttggatttg tggtatccca taccactaga tttcctcgtc              400
ctatggaacg agaaggtgtc gactaccatt acgttaacag agaggcc                 447

<210> SEQ ID NO 10
<211> LENGTH: 40
<212> TYPE: DNA
<213> ORGANISM: artificial sequence
<220> FEATURE:
<223> OTHER INFORMATION: primer P3

<400> SEQUENCE: 10
gatacctatc acggagaaat tagatcctga tagaatcgcg                          40

<210> SEQ ID NO 11
<211> LENGTH: 22
<212> TYPE: DNA
<213> ORGANISM: artificial sequence
<220> FEATURE:
<223> OTHER INFORMATION: primer P1

<400> SEQUENCE: 11
attaaacgca aatatccatg gg                                             22

<210> SEQ ID NO 12
<211> LENGTH: 27
<212> TYPE: DNA
<213> ORGANISM: artificial sequence
<220> FEATURE:
<223> OTHER INFORMATION: primer F2

<400> SEQUENCE: 12
gcggtaccct ggggttaggc gatagag                                        27

<210> SEQ ID NO 13
<211> LENGTH: 20
<212> TYPE: DNA
<213> ORGANISM: artificial sequence
```

-continued

<220> FEATURE:
<223> OTHER INFORMATION: primer P5

<400> SEQUENCE: 13 attttctccgt gataggtatc 20

<210> SEQ ID NO 14
<211> LENGTH: 22
<212> TYPE: DNA
<213> ORGANISM: artificial sequence
<220> FEATURE:
<223> OTHER INFORMATION: primer P5

<400> SEQUENCE: 14
ggcctctctg ttaacgtaat gg 22

<210> SEQ ID NO 15
<211> LENGTH: 22
<212> TYPE: DNA
<213> ORGANISM: artificial sequence
<220> FEATURE:
<223> OTHER INFORMATION: primer P2

<400> SEQUENCE: 15
gcgtcgaagt ttgagcatgt gc 22

<210> SEQ ID NO 16
<211> LENGTH: 40
<212> TYPE: DNA
<213> ORGANISM: artificial sequence
<220> FEATURE:
<223> OTHER INFORMATION: primer P4

<400> SEQUENCE: 16
ctctagcgcc taaccccagg cgaccgacga caacctttat 40

<210> SEQ ID NO 17
<211> LENGTH: 840
<212> TYPE: DNA
<213> ORGANISM: feline infectious peritonitis virus
<220> FEATURE:
<223> OTHER INFORMATION:

<400> SEQUENCE: 17
aaaccaaggc atataatccc gacgaagcat ttttggtttg aactaaacaa a 51 atg aag tac att ttg cta ata ctc gcg tgc ata att gca tgc gtt 96
Met Lys Tyr Ile Leu Leu Ile Leu Ala Cys Ile Ile Ala Cys Val
1 5 10 15 tat ggt gaa cgc tac tgt gcc atg caa gac agt ggc ttg cag tgt 141
Tyr Gly Glu Arg Tyr Cys Ala Met Gln Asp Ser Gly Leu Gln Cys
20 25 30 att aat ggc aca aat tca aga tgt caa acc tgc ttt gaa cgt ggt 186
Ile Gln Gly Thr Gln Ser Arg Cys Gln Thr Cys Phe Glu Arg Gly
35 40 45 gat ctt att tgg cat ctt gct aac tgg aac ttc agc tgg tct gta 231
Asp Leu Ile Trp His Leu Ala Asn Trp Asn Phe Ser Trp Ser Val
50 55 60 ata ttg att gtt ttt ata aca gtg tta caa tat ggc aga cca caa 276
Ile Leu Ile Val Phe Ile Thr Val Leu Gln Tyr Gly Arg Pro Gln
65 70 75 ttt agc tgg ctc gtt tat ggc att aaa atg ctg atc atg tgg cta 321
Phe Ser Trp Leu Val Tyr Gly Ile Lys Met Leu Ile Met Trp Leu
80 85 90

-continued

```
tta tgg cct att gtt cta gcg ctt acg att ttt aat gca tac tct          366
Leu Trp Pro Ile Val Leu Ala Leu Thr Ile Phe Asn Ala Tyr Ser
                 95                 100                 105 gag tac caa gtt tcc aga tat gta atg ttc ggc ttt agt gtt gca          411
Glu Tyr Gln Val Ser Arg Tyr Val Met Phe Gly Phe Ser Val Ala
                110                 115                 120 ggt gca gtt gta acg ttt gca ctt tgg atg atg tat ttt gtg aga          456
Gly Ala Val Val Thr Phe Ala Leu Trp Met Met Tyr Phe Val Arg
                125                 130                 135 tct gtt cag cta tat aga aga acc aaa tca tgg tgg tct ttt aat          501
Ser Val Gln Leu Tyr Arg Arg Thr Lys Ser Trp Trp Ser Phe Asn
                140                 145                 150 cct gag act aat gca att ctt tgt gtt aat gca ttg ggt aga agt          546
Pro Glu Thr Asn Ala Ile Leu Cys Val Asn Ala Leu Gly Arg Ser
                155                 160                 165 tat gtg ctt ccc tta gat ggt act cct aca ggt gtt acc ctt act          591
Tyr Val Leu Pro Leu Asp Gly Thr Pro Thr Gly Val Thr Leu Thr
                170                 175                 180 cta ctt tca gga aat cta tat gct gaa ggt ttc aaa atg gct ggt          636
Leu Leu Ser Gly Asn Leu Tyr Ala Glu Gly Phe Lys Met Ala Gly
                185                 190                 195 ggt tta acc atc gag cat ttg cct aaa tac gtc atg att gct aca          681
Gly Leu Thr Ile Glu His Leu Pro Lys Tyr Val Met Ile Ala Thr
                200                 205                 210 cct agt aga acc atc gtt tat aca tta gtt gga aaa caa tta aaa          726
Pro Ser Arg Thr Ile Val Tyr Thr Ile Val Gly Lys Gln Leu Lys
                215                 220                 225 gca act act gcc aca gga tgg gct tac tac gta aaa tct aaa gct          771
Ala Thr Thr Ala Thr Gly Trp Ala Tyr Tyr Val Lys Ser Lys Ala
                230                 235                 240 ggt gat tac tca aca gaa gca cgt act gac aat ttg agt gaa cat          816
Gly Asp Tyr Ser Thr Glu Ala Arg Thr Asp Asn Leu Ser Glu His
                245                 250                 255 gaa aaa tta tta cat atg gtg taa                                      840
Glu Lys Leu Leu His Met Val
                260

<210> SEQ ID NO 18
<211> LENGTH: 1144
<212> TYPE: DNA
<213> ORGANISM: feline infectious peritonitis virus
<220> FEATURE:
<223> OTHER INFORMATION:

<400> SEQUENCE: 18 atg gcc aca cag gga caa cgc gtc aac tgg gga gat gaa cct tcc           45
Met Ala Thr Gln Gly Gln Arg Val Asn Trp Gly Asp Glu Pro Ser
  1               5                  10                  15 aaa aga cgt ggt cgt tct aac tct cgt ggt cgg aag aat aat gat           90
Lys Arg Arg Gly Arg Ser Asn Ser Arg Gly Arg Lys Asn Asn Asp
                 20                  25                  30 ata cct ttg tca ttc tac aac ccc att acc ctc gaa caa gga tct          135
Ile Pro Leu Ser Phe Tyr Asn Phe Ile Thr Leu Glu Gln Glu Ser
                 35                  40                  45 aaa ttt tgg aat tta tgt ccg aga gac ctt gtt ccc aaa gga ata          180
Lys Phe Trp Asn Leu Cys Pro Arg Asp Leu Val Pro Lys Gly Ile
                 50                  55                  60 ggt aat aag gat caa caa att ggt tat tgg aat aga cag att cgt          225
Gly Asn Lys Asp Gln Gln Ile Gly Tyr Trp Asn Arg Gln Ile Arg
                 65                  70                  75 tat cgt att gta aaa ggc cag cgt aag gaa ctc gct gag agg tgg          270
```

-continued

```
Tyr Arg Ile Val Lys Gly Gln Arg Lys Glu Leu Ala Glu Arg Trp
                80              85                  90 ttc ttt tac ttc tta ggt aca gga cct cat gct gat gct aaa ttc         315
Phe Phe Tyr Phe Leu Gly Thr Gly Phe His Ala Asp Ala Lys Phe
                95              100                 105 aaa gac aag att gat gga gtc ttc tgg gtt gca agg gat ggt gcc         360
Lys Asp Lys Ile Asp Gly Val Phe Trp Val Ala Arg Asp Gly Ala
                110             115                 120 atg aac aag ccc aca acg ctt ggc act cgt gga acc aat aac gaa         405
Met Asn Lys Pro Thr Thr Leu Gly Thr Arg Gly Thr Asn Asn Glu
                125             130                 135 tcc aaa cca ctg aga ttt gat ggt aag ata ccg cca cag ttt cag         450
Ser Lys Pro Leu Arg Phe Asp Gly Lys Ile Pro Pro Gln Phe Gln
                140             145                 150 ctt gaa gtg aac cgt tct agg aac aat tca agg tct ggt tct cag         495
Leu Glu Val Asn Arg Ser Arg Asn Asn Ser Arg Ser Gly Ser Gln
                155             160                 165 tct aga tct gtt tca aga aac aga tct caa tct aga gga aga cac         540
Ser Arg Ser Val Ser Arg Asn Arg Ser Gln Ser Arg Gly Arg His
                170             175                 180 cat tcc aat aac cag aat aat aat gtt gag gat aca att gta gcc         585
His Ser Asn Asn Gln Asn Asn Asn Val Glu Asp Thr Ile Val Ala
                185             190                 195 gtg ctt gaa aaa tta ggt gtt act gac aaa caa agg tca cgt tct         630
Val Leu Glu Lys Leu Gly Val Thr Asp Lys Gln Arg Ser Arg Ser
                200             205                 210 aaa cct aga gaa cgt agt gat tcc aaa cct agg gac aca aca cct         675
Lys Pro Arg Glu Arg Ser Asp Ser Lys Pro Arg Asp Thr Thr Pro
                215             220                 225 aag aat gcc aac aaa cac acc tgg aag aaa act gca ggc aag gga         720
Lys Asn Ala Asn Lys His Thr Trp Lys Lys Thr Ala Gly Lys Gly
                230             235                 240 gat gtg aca act ttc tat ggt gct aga agt agt tca gct aac ttt         765
Asp Val Thr Thr Phe Tyr Gly Ala Arg Ser Ser Ser Ala Asn Phe
                245             250                 255 ggt gat agt gat ctc gtt gcc aat ggt aac gct gcc aaa tgc tac         810
Gly Asp Ser Asp Leu Val Ala Asn Gly Asn Ala Ala Lys Cys Tyr
                260             265                 270 cct cag ata gct gaa tgt gtt cca tca gtg tct agc ata atc ttt         855
Pro Gln Ile Ala Glu Cys Val Pro Ser Val Ser Ser Ile Ile Phe
                275             280                 285 ggc agt caa tgg tct gct gaa gaa gct ggt gat caa gtg aaa gtc         900
Gly Ser Gln Trp Ser Ala Glu Glu Ala Gly Asp Gln Val Lys Val
                290             295                 300 acg ctc act cac acc tac tac ctg cca aag gat gat gcc aaa act         945
Thr Leu Thr His Thr Tyr Tyr Leu Pro Lys Asp Asp Ala Lys Thr
                305             310                 315 agt caa ttc cta gaa cag att gac gct tac aag cga cct tct gaa         990
Ser Gln Phe Leu Glu Gln Ile Asp Ala Tyr Lys Atg Pro Ser Glu
                320             325                 330 gtg gct aag gat cag agg caa aga aga tcc cgt tct aag tct gct        1035
Val Ala Lys Asp Gln Arg Gln Arg Arg Ser Arg Ser Lys Ser Ala
                335             340                 345 gat aag aag cct gag gag ttg tct gta act ctt gtg gag gca tac        1080
Asp Lys Lys Pro Glu Glu Lys Ser Val Thr Leu Val Glu Ala Tyr
                350             355                 360 aca gat gtg ttt gat gac aca cag gtt gag atg att gat gag gtt        1125
Thr Asp Val Phe Asp Asp Thr Gln Val Glu Met Ile Asp Glu Val
                365             370                 375
```

```
                                                        -continued acg aac taa acgcatgctc                                                 1144
Thr Asn <210> SEQ ID NO 19
<211> LENGTH: 1979
<212> TYPE: DNA
<213> ORGANISM: feline leukemia virus
<220> FEATURE:
<223> OTHER INFORMATION:

<400> SEQUENCE: 19
accaccaatc aagacctctc ggacagcccc agctcagacg atccatcaag                   50 atg gaa agt cca acg cac cca aaa ccc tct aaa gat aag act ctc              95
Met Glu Ser Pro Thr His Pro Lys Pro Ser Lys Asp Lys Thr Leu
  1               5                  10                  15 tcg tgg aac tta gcg ttt ctg gtg ggg atc tta ttt aca ata gac             140
Ser Trp Asn Leu Ala Phe Leu Val Gly Ile Leu Phe Thr Ile Asp
                 20                  25                  30 ata gga atg gcc aat cct agt cca cac caa ata tat aat gta act             185
Ile Gly Met Ala Asn Pro Ser Pro His Gln Ile Tyr Asn Val Thr
             35                  40                  45 tgg gta ata acc aat gta caa act aac acc caa gct aac gcc acc             230
Trp Val Ile Thr Asn Val Gln Thr Asn Thr Gln Ala Asn Ala Thr
         50                  55                  60 tct atg tta gga acc tta acc gat gcc tac cct acc cta cat gtt             275
Ser Met Leu Gly Thr Leu Thr Asp Ala Tyr Pro Thr Leu His Val
     65                  70                  75 gac tta tgt gac cta gtg gga gac acc tgg gaa cct ata gtc cta             320
Asp Leu Cys Asp Leu Val Gly Asp Thr Trp Glu Pro Ile Val Leu
 80                  85                  90 aac cca acc aat gta aaa cac ggg gca cgt tac tcc tcc tca aaa             365
Asn Pro Thr Asn Val Lys His Gly Ala Arg Tyr Ser Ser Ser Lys
                 95                 100                 105 tat gga tgt aaa act aca gat aga aaa aaa cag caa cag aca tac             410
Tyr Gly Cys Lys Thr Thr Asp Arg Lys Lys Gln Gln Gln Thr Tyr
             110                 115                 120 ccc ttt tac gtc tgc ccc gga cat gcc ccc tcg ttg ggg cca aag             455
Pro Phe Tyr Val Cys Pro Gly His Ala Pro Ser Leu Gly Pro Lys
         125                 130                 135 gga aca cat tgt gga ggg gca caa gat ggg ttt tgt gcc gca tgg             500
Gly Thr His Cys Gly Gly Ala Gln Asp Gly Phe Cys Ala Ala Trp
     140                 145                 150 gga tgt gag acc acc gga gaa gct tgg tgg aag ccc acc tcc tca             545
Gly Cys Glu Thr Thr Gly Glu Ala Trp Trp Lys Pro Thr Ser Ser
 155                 160                 165 tgg gac tat atc aca gta aaa aga ggg agt agt cag gac aat agc             590
Trp Asp Tyr Ile Thr Val Lys Arg Gly Ser Ser Gln Asp Asn Ser
                 170                 175                 180 tgt gag gga aaa tgc aac ccc ctg gtt ttg cag ttc acc cag aag             635
Cys Glu Gly Lys Cys Asn Pro Leu Val Leu Gln Phe Thr Gln Lys
             185                 190                 195 gga aga caa gcc tct tgg gac gga cct aag atg tgg gga ttg cga             680
Gly Arg Gln Ala Ser Trp Asp Gly Pro Lys Met Trp Gly Leu Arg
         200                 205                 210 cta tac cgt aca gga tat gac cct atc gct tta ttc acg gtg tcc             725
Leu Tyr Arg Thr Gly Tyr Asp Pro Ile Ala Leu Phe Thr Val Ser
     215                 220                 225 cgg cag gta tca acc att acg ccg cct cag gca atg gga cca aac             770
Arg Gln Val Ser Thr Ile Thr Pro Pro Gln Ala Met Gly Pro Asn
 230                 235                 240
```

```
                                    -continued cta gtc tta cct gat caa aaa ccc cca tcc cga caa tct caa aca         815
Leu Val Leu Pro Asp Gln Lys Pro Pro Ser Arg Gln Ser Gln Thr
                245                 250                 255 ggg tcc aaa gtg gcg acc cag agg ccc caa acg aat gaa agc gcc         860
Gly Ser Lys Val Ala Thr Gln Arg Pro Gln Thr Asn Glu Ser Ala
        260                 265                 270 cca agg tct gtt gcc ccc acc acc atg ggt ccc aaa cgg att ggg         905
Pro Arg Ser Val Ala Pro Thr Thr Met Gly Pro Lys Arg Ile Gly
    275                 280                 285 acc gga gat agg tta ata aat tta gta caa ggg aca tac cta gcc         950
Thr Gly Asp Arg Leu Ile Asn Leu Val Gln Gly Thr Tyr Leu Ala
290                 295                 300 tta aat gcc acc gac ccc aac aaa act aaa gac tgt tgg ctc tgc         995
Leu Asn Ala Thr Asp Pro Asn Lys Thr Lys Asp Cys Trp Leu Cys
                305                 310                 315 ctg gtt tct cga cca ccc tat tac gaa ggg att gca atc tta ggt        1040
Leu Val Ser Arg Pro Pro Tyr Tyr Glu Gly Ile Ala Ile Leu Gly
        320                 325                 330 acc tac agc aac caa aca aac ccc ccc cca tcc tgc cta tct act        1085
Thr Tyr Ser Asn Gln Thr Asn Pro Pro Pro Ser Cys Leu Ser Ile
    335                 340                 345 ccg caa cac aaa cta act ata tct gaa gta tca ggg caa gga atg        1130
Pro Gln His Lys Leu Thr Ile Ser Glu Val Ser Gly Gln Gly Met
350                 355                 360 tgc ata ggg act gtt cct aaa acc cac cag gct ttg tgc aat aag        1175
Cys Ile Gly Thr Val Pro Lys Thr His Gln Ala Leu Cys Asn Lys
                365                 370                 375 aca caa cag gga cat aca ggg gcg cac tat cta gcc gcc ccc aac        1220
Thr Gln Gln Gly His Thr Gly Ala His Tyr Leu Ala Ala Pro Asn
        380                 385                 390 ggc acc tat tgg gcc tgt aac act gga ctc acc cca tgc att tcc        1265
Gly Thr Tyr Trp Ala Cys Asn Thr Gly Leu Thr Pro Cys Ile Ser
    395                 400                 405 atg gcg gtg ctc aat tgg acc tct gat ttt tgt gtc tta atc gaa        1310
Met Ala Val Leu Asn Trp Thr Ser Asp Phe Cys Val Leu Ile Glu
410                 415                 420 tta tgg ccc aga gtg act tac cat caa ccc gaa tat gtg tac aca        1355
Leu Trp Pro Arg Val Thr Tyr His Gln Pro Glu Tyr Val Tyr Thr
                425                 430                 435 cat ttt gcc aaa gct gtc agg ttc cga aga gaa cca ata tca cta        1400
His Phe Ala Lys Ala Val Arg Phe Arg Arg Glu Pro Ile Ser Leu
        440                 445                 450 acg gtt gcc ctt atg ttg gga gga ctt act gta ggg ggc ata gcc        1445
Thr Val Ala Leu Met Leu Gly Gly Leu Thr Val Gly Gly Ile Ala
    455                 460                 465 gcg ggg gtc gga aca ggg act aaa gcc ctc ctt gaa aca gcc cag        1490
Ala Gly Val Gly Thr Gly Thr Lys Ala Leu Leu Glu Thr Ala Gln
470                 475                 480 ttc aga caa cta caa atg gcc atg cac aca gac atc cag gcc cta        1535
Phe Arg Gln Leu Gln Met Ala Met His Thr Asp Ile Gln Ala Leu
                485                 490                 495 gaa gaa tca att agt gcc tta gaa aag tcc ctg acc tcc ctt tct        1580
Glu Glu Ser Ile Ser Ala Leu Glu Lys Ser Leu Thr Ser Leu Ser
        500                 505                 510 gaa gta gtc tta caa aac aga cgg ggc cta gat att cta ttc tta        1625
Glu Val Val Leu Gln Asn Arg Arg Gly Leu Asp Ile Leu Phe Leu
    515                 520                 525 caa gag gga ggg ctc tgt gcc gca ttg aaa gaa gaa tgt tgc ttc        1670
Gln Glu Gly Gly Leu Cys Ala Ala Leu Lys Glu Glu Cys Cys Phe
530                 535                 540
```

```
tat gcg gat cac acc gga ctc gtc cga gac aat atg gcc aaa tta       1715
Tyr Ala Asp His Thr Gly Leu Val Arg Asp Asn Met Ala Lys Leu
                545                 550                 555 aga gaa aga cta aaa cag cgg caa caa ctg ttt gac tcc caa cag       1760
Arg Glu Arg Leu Lys Gln Arg Gln Gln Leu Phe Asp Ser Gln Gln
                560                 565                 570 gga tgg ttt gaa gga tgg ttc aac aag tcc ccc tgg ttt aca acc       1805
Gly Trp Phe Glu Gly Trp Phe Asn Lys Ser Pro Trp Phe Thr Thr
                575                 580                 585 cta att tcc tcc att atg ggc ccc tta cta atc cta ctc cta att       1850
Leu Ile Ser Ser Ile Met Gly Pro Leu Leu Ile Leu Leu Leu Ile
                590                 595                 600 ctc ctc ttc ggc cca tgc atc ctt aac cga tta gta caa ttc gta       1895
Leu Leu Phe Gly Pro Cys Ile Leu Asn Arg Leu Val Gln Phe Val
                605                 610                 615 aaa gac aga ata tct gtg gta cag gct tta att tta acc caa cag       1940
Lys Asp Arg Ile Ser Val Val Gln Ala Leu Ile Leu Thr Gln Gln
                620                 625                 630 tac caa cag ata aag caa tac gat ccg gac cga cca tga               1979
Tyr Gln Gln Ile Lys Gln Tyr Asp Pro Asp Arg Pro
                635                 640
```

RECOMBINANT MULTIVALENT VIRAL VACCINE

This application is a continuation of U.S. application Ser. No. 08/552,369 filed on Nov. 3, 1995 now U.S. Pat. No. 6,241,989, which is a continuation-in-part of U.S. application Ser. No. 08/190,789, filed Jan. 27, 1994, now abandoned, which is a continuation of U.S. application Ser. No. 07/726,609, filed Jul. 9, 1991, now abandoned, the disclosures of which are incorporated herein by reference.

FIELD OF THE INVENTION

The present invention relates generally to the production and use of a recombinant viral vector as a multivalent vaccine in the protection of felines against infection by various viral pathogens of felines. More particularly, the present invention relates to a recombinant multivalent vaccine formed by inserting multiple genes such as a feline panleukopenia virus (FPV) gene, a rabies virus gene, and/or a feline calicivirus (FCV) capsid protein gene each operably linked to a promoter, into a raccoon poxvirus (RCNV) for expression.

BACKGROUND OF THE INVENTION

1. Feline Panleukopenia Virus Biology and Pathology

Feline panleukopenia virus (FPV) is a highly contagious viral disease of domestic cats and exotic cats. The virus is transmittable to susceptible cats by contact with body secretions and excretions of infected cats during the acute phase of infection in which virus is shed. Aerosol transmission, and transmission by insect vectors can also occur. The virus infects and destroys actively replicating cells in lymph nodes, and hematopoietic and gastrointestinal tissues of felines thereby causing sudden onset of symptoms including fever, anorexia, leukopenia, vomiting and diarrhea. In particular, FPV causes severe clinical illness in young kittens with high morbidity and mortality. A marked drop in total leukocyte count by day 4 to 6 after infection is the prominent indicator of FPV infection. Disease caused by infection with FPV has been described as feline parvovirus, feline panleukopenia, infectious enteritis, viral enteritis, cat "distemper", granulocytosis, cat plague, and cat fever.

FPV is a small, single stranded DNA virus, a parvovirus, that requires rapidly multiplying cells for DNA replication. The genome of FPV is a linear, single stranded DNA of about 5 kilobases in size that encodes three structural proteins: a large 80–85 kilodalton (kd) protein ("VP1") comprising 10% to 15% of the viral protein; a medium size protein of 64–67 kd ("VP2"); and a part of the VP2 protein which is converted to a 60–64 kd protein ("VP3") by proteolytic cleavage. The three proteins physically form a nested set of proteins within which the viral DNA is enclosed. FPV is very closely related to canine parvovirus (CPV) and mink enteritis virus both on the protein and amino acid level (Tratschin et al., 1982, *J. Gen. Virol.*, 61:33–41; Truyen et al., 1994, *Virology* 200:494–503; and Truyen et al., 1994, *J. Virol.* 66:5399–5408). The high cross-reactivity between CPV and FPV indicated their antigenic similarities and the possibility of mutual neutralization and protection between the two viruses.

2. Rabies Virus Biology and Pathology

Rabies virus is a member of the genus *Lyssavirus* in the family Rhabdoviridae, and contains an unsegmented negative stranded RNA genome. Of the five known viral structural proteins, the rabies virus transmembrane glycoprotein G plays a critical role for the induction and binding of the virusneutralization antibodies and the stimulation of T cell-mediated immunity (Lafon et al., 1983, *J. Gen. Virol.* 64:843–851; Lafon et al., 1985, *J. Gen. Virol.* 66:2125–2133; Wiktor et al., 1973, *J. Immunol.* 110:269–276; Wiktor et al., 1984, *Dev. Biol. Stand.* 57:199–211; Wiktor et al., 1984, *Proc. Natl. Acad. Sci. U.S.A.* 81:7194–7198). Also, the arginine, at position 333 in the glycoprotein amino acid sequence, is essential for the integrity of at least one antigenic determinant and for the ability of rabies virus to produce a lethal infection in adult mice (Dietzschold et al., 1983, *Proc. Natl. Acad. Sci. U.S.A.* 80:7074). Initial symptoms of rabies virus infection include fever, and malaise. The disease progresses rapidly to symptoms including agitation, convulsions, and coma; and eventually, if untreated, the infected animal may die from organ failure.

3. Recombinant Veterinary Vaccines

In the art of veterinary vaccines, purified recombinant VP2 protein has been used as an immunogen for protecting dogs against infection by canine parvovirus (Wood et al., U.S. Pat. No. 4,971,793). In terms of viral vaccine vectors, vaccinia virus recombinants have been constructed with insertion of a respective gene encoding either feline infectious peritonitis virus (FIPV) spike protein, membrane glycoprotein, or nucleocapsid protein (Vennema et al., 1990, *J. Virol.* 64:1407–1409; Vennema et al., 1991, *Virology* 181:327–335). Immunization with such a vaccinia virus recombinant appeared to be of little or no value in the protection of vaccinated kittens against challenge with FIPV. Thus, vaccinia virus vectors do not appear to be a good choice for constructing feline recombinant vaccines because: (a) vaccinia virus/viral vectors did not elicit protection or detectable virus neutralization antibodies (Vennema et al., 1991, supra; Scott, 1988, *Conf. Res. Workers Anim. Dis.* 69:60); and (b) of concerns of introducing recombinant vaccinia virus for veterinary or human use, particularly because of rare side effects associated with vaccinia virus immunization.

In contrast, a raccoon poxvirus (RCNV) recombinant vector containing the gene encoding rabies virus surface glycoprotein G, has been used successfully to induce immunity in raccoons which is protective against subsequent challenge with raccoon rabies virus (Esposito et al., 1988, *Virology*, 165:313316). However, the investigators report that the complete host range of RCNV is not known. A recombinant RCNV containing the gene encoding FPV VP2 protein ("recombinant RCNV/FPV") was recently constructed by inserting the VP2 protein gene into a vaccinia expression vector, and then recombining the insertion into the thymidine kinase (TK) gene of RCNV. In a vaccine trial, all cats immunized with the RCNV/FPV were fully protected against subsequent FPV challenge, and showed high titers of FPV viral neutralization antibody (U.S. patent application Ser. No. 08/190,789 assigned to the assignee of the present invention). Presently, there are no reports of the design of a functional multivalent RCNV-vectored vaccine, and its use for inducing protective immunity in felines.

SUMMARY OF THE INVENTION

A novel raccoon poxvirus (RCNV) recombinant vaccine against both feline panleukopenia virus (FPV) and rabies virus was developed based on the homologous thymidine kinase gene between vaccinia virus and RCNV. The infectious recombinant virus (RCNV/FPV/RAB) carried both FPV VP2 and rabies G protein genes, each operably linked to a promoter. Vaccine trials using RCNV/FPV/RAB induced strong immune responses in cats to both FPV and rabies virus. Cats immunized with RCNV/FPV/RAB were fully protected against subsequent FPV challenge. Viral neutralization antibody titers for both FPV and rabies virus were sufficient to protect cats from the related virulent virus infection or challenge. In another embodiment, a novel raccoon poxvirus multivalent recombinant vaccine can be developed based on an insertion vector being constructed to have homologous hemagglutinin (HA) gene sequences which flank one or more inserted genes (such as FCV capsid protein gene), and thus allowing recombination into the hemagglutinin gene sequences of raccoon poxvirus. Thus, the methods and compositions of the present invention provide the basis for producing novel multivalent recombinant vaccine vectors for felines. Using the methods according to the present invention, a multivalent recombinant raccoon poxvirus could have the following insertions: one or more exogenous genes recombined into both the raccoon poxvirus TK and HA gene sequences; more than one exogenous gene recombined into the raccoon poxvirus TK gene sequences; and more than one exogenous gene recombined into the raccoon poxvirus HA gene sequences.

Accordingly, it is one object of the present invention to provide a method for inserting more than one exogenous gene into the thymidine kinase gene region and/or hemagglutinin gene region of raccoon poxvirus for expression.

It is another object of the present invention to provide a method for inserting multiple genes encoding antigens of feline pathogens into the thymidine kinase gene region and/or hemagglutinin gene region of raccoon poxvirus for expression.

It is a further object of the invention to provide vaccine compositions, comprising recombinant raccoon poxvirus, for eliciting a protective immune response, to more than one feline pathogen, in felines receiving the vaccine compositions.

These and other objects of the present invention will become readily apparent from the ensuing description, embodiments and illustrations.

BRIEF DESCRIPTION OF THE FIGURES

FIG. 6 is a diagram of the cloning of feline calicivirus (FCV) capsid protein gene and construction of a raccoon poxvirus hemagglutinin gene (HA) insertion vector carrying the FCV capsid protein gene.

FIG. 6B is a schematic showing construction of a fragment containing the FCV capsid gene operably linked to a promoter, and cloning the fragment into plasmid pGEM-3Z in forming a raccoon poxvirus HA insertion vector termed pGEM/HA/FCV.

FIG. 7 shows immunofluorescent antibody staining of cells infected by a recombinant raccoon poxvirus containing the FCV capsid protein gene.

DETAILED DESCRIPTION OF THE INVENTION

Figure 1:
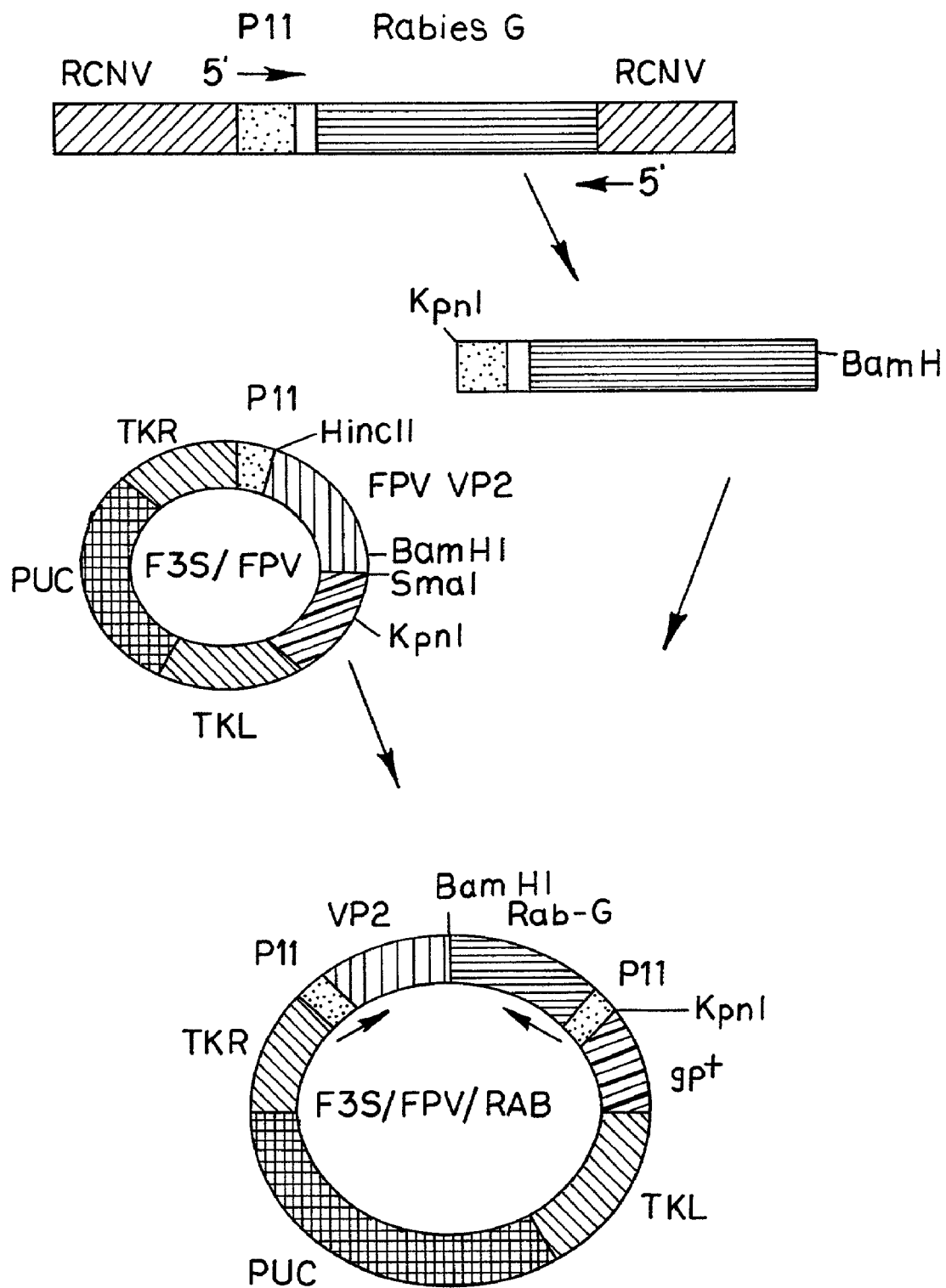
FIG. 1 is a diagram showing the insertion of a rabies-G protein gene, operably linked to a vaccinia virus $P_{11}$ late promoter, into a recombinant vaccinia virus recombinant plasmid carrying the FPV VP2 gene, operably linked to a vaccinia virus $P_{11}$ late promoter, in forming a novel plasmid termed F3S/FPV/RAB.

The present invention provides a method for constructing recombinant RCNV which have incorporated into the viral thymidine kinase gene region and/or hemagglutinin gene region multiple exogenous genes encoding antigens of various feline pathogens. Also provided are vaccine compositions comprising the recombinant RCNV, and a method of using the vaccine compositions to elicit a protective immune response in immunized felines.

Definitions

"Expression cassette" is a term used herein for the purposes of the specification and claims to refer to a recombinant nucleic acid molecule containing multiple genes, each encoding an antigen of a feline pathogen, which are operably linked to one or more promoters such that when the expression cassette is inserted into RCNV, and upon subsequent infection of feline cells with the recombinant RCNV, the antigens encoded by their respective gene are produced by the infected feline cells.

"Feline pathogen" is a term used herein for the purposes of the specification and claims to refer to one or more microorganisms which are natural pathogens of cats, and include rabies virus, feline panleukopenia virus (FPV), feline *Chlamydia*, feline immunodeficiency virus (FIV), feline leukemia virus (FeLV), feline infectious peritonitis virus (FIPV), calicivirus, and feline herpesvirus (FHV).

The method of the present invention first comprises ligating an expression cassette into the thymidine kinase (TK) gene contained into an insertion vector such as a vaccinia virus (VV) expression vector. Because of the sequence homology between VV TK gene and the RCNV TK gene, the expression cassette within the VV expression vector, and flanking VV TK gene sequence, is then recombined into the TK gene of raccoon poxvirus (RCNV). Alternatively, an expression cassette can be ligated into an insertion vector which has HA sequences flanking the insertion which are sufficiently homologous to promote recombination of the expression cassette into the HA gene of raccoon poxvirus. In either instance, the resultant recombinant virus can then be used as a vaccine composition in a method for immunizing felines against challenge by those feline pathogens, antigens of which are encoded by the expression cassette in the recombinant virus. For purposes of illustration and description, but not limitation, in one embodiment of the present invention the FPV VP2 gene, and the rabies virus G protein gene were each separately and operably linked to a VV late promoter in forming an expression cassette which was then recombined into raccoon poxvirus. However, the methods of the present invention provide a way to insert other exogenous genes into the raccoon poxvirus for expression upon infection into a susceptible host cell. Thus, the present invention includes compositions comprising a combination of two or more genes encoding antigens found in one or more species/strains of feline pathogens, as will be illustrated in the following embodiments:

EXAMPLE 1

Construction of a Recombinant Insertion Plasmid

The essential features of an insertion plasmid that is useful in the method of the present invention include the following features.

(a) The plasmid sequences flanking the insertion site into which are to be inserted multiple genes, contain sequences which have sufficient homology with sequences present in the raccoon poxvirus genome to mediate recombination. For example, a plasmid comprised of vaccinia virus sequences is used, wherein the site for insertion of multiple genes (inserted as an expression cassette) is flanked by vaccinia virus thymidine kinase gene sequences. The nucleotide sequence of the TK gene of VV is not identical to the nucleotide sequence of the TK gene of raccoon poxvirus; however, there is a sufficient degree of identity ("homology") to promote hybridization of the TK gene sequence of VV to the TK gene sequence of raccoon poxvirus and subsequent recombination. Thus, multiple genes flanked by TK gene sequence of VV are subsequently recombined into the TK gene of raccoon poxvirus. Alternatively, such flanking sequences can be part of the insert to be inserted into the plasmid.

(b) The flanking sequences must be homologous to a region of the raccoon poxvirus (into which the multiple genes are recombined) that is nonessential for the growth and propagation of the raccoon poxvirus. For example, it was found, as illustrated in Examples 2, 6 and 8–10, that both the TK gene and the hemagglutinin (HA) gene of the raccoon poxvirus genome can be used for insertion of exogenous genes by recombination. Insertion of exogenous genes into both or either of the TK gene or HA gene by recombination results in recombinant raccoon poxvirus capable of infection and replication, and can be used for expression of the recombined exogenous genes in host cells infected with the recombinant virus.

Desirable features of an insertion vector that is useful in the method of the present invention include the following features.

(a) Although it is possible that exogenous genes recombined into the raccoon poxvirus genome may be expressed without first operably linking the genes with one or more control element elements for expression (such as a promoter) prior to recombination, operably linking the control element(s) to the multiple genes (thereby forming an expression cassette) before using the genes for insertion into the plasmid insertion vector, will likely result in higher efficiency of expression of the recombined genes. Alternatively, the sequences flanking the insertion site of the plasmid insertion vector can be engineered to contain control elements which are then operably linked to the multiple genes upon insertion.

(b) Although one promoter may be used to drive the expression of two exogenous genes to be recombined, use of two promoters in an insertion vector, each promoter operably linked to an individual exogenous gene, will provide higher efficiency of expression.

To illustrate this embodiment, first an recombinant insertion plasmid was constructed by inserting a 2,304 base pair (bp) fragment containing the FPV VP2 gene (nucleotides 1–1752 of SEQ ID NO:1), from infectious FPV genomic DNA, into a VV insertion vector. The 2,304 base pair (bp) fragment was released from the infectious clone by digestion with restriction enzyme HincII and SmaI. A VV insertion vector, pTKgptF3S (Baroudy et al., 1980, *J. Biol. Chem.* 255:4372–4380), was digested with HincII, treated with calf intestinal phosphatase, purified, and ligated with the FPV VP2 DNA. The ligation mixture was used to transform *Escherichia coli* DH5 alpha. The transformed *E. coli* cells were plated on Lauria broth (LB) agar plates with 50 µg/ml ampicillin and incubated overnight at 37° C. The colonies grown on the agar plates were screened by in situ colony hybridization using a $^{32}$P-labeled FPV VP2 probe. The correct orientation and the proper open reading frame were further confirmed by restriction enzyme mapping and DNA sequencing. A plasmid, termed F3S/FPV, contained the VP2 gene in the correct orientation in relation to the operably linked VV $P_{11}$ promoter.

A DNA fragment containing the rabies-G gene (SEQ ID NO:2) operably linked to a VV $P_{11}$ promoter (SEQ ID NO:3) was purified from a RCNV rabies-G recombinant virus described previously (Ngichabe, C. K., 1992, Ph.D. Thesis, Cornell University, Ithaca, N.Y.). The RCNV rabies-G recombinant virus was grown in CV-1 cell monolayers. When the cytopathic effect (CPE) reached about 80% of the cell monolayer, the cells were scraped off, washed in PBS with 100 µM MgSO$_4$ (PBS-M) and resuspended in 1,200 µp of PBS-M. The virus was released from the infected cells by denaturation solution (0.5% Triton, 45 mM mercaptoethanol and 20 mM EDTA). The cell lysate was centrifuged at 300×g to separate the chromosomal DNA and debris, then the viruses were pelleted from the supernatant by centrifugation at top speed of the microcentrifuge for 10 minutes, and suspended in 100 µl of Tris-EDTA buffer (TE), pH 7.5. After treatment with 150 µg/ml proteinase K, 200 mM NaCl, and 45 mM mercaptoethanol. The mixture was mixed gently and incubated for 2 hours in a 50° C. waterbath. After extraction twice with equal volume of Tris buffered phenol:chloroform: isoamyl alcohol and four times with water saturated ether and ethanol precipitation. The DNA was pelleted by centrifugation at top speed at 4° C. in a microcentrifuge, washed in 70% cold alcohol, resuspended in 100 µl of water and then stored at −70° C. for use.

A DNA fragment containing the gene encoding rabies-G was isolated, and cloned into F3S/FPV, as follows (See also FIG. 1). A 1.75 Kb fragment containing the rabies-G gene operably linked to a $P_{11}$ late promoter was amplified by polymerase chain reaction (PCR) from purified RCNV rabies-G recombinant virus DNA using a forward primer (SEQ ID NO:4) and a reverse primer (SEQ ID NO:5). After separation of the amplified DNA on 1% agarose gel, the amplified DNA was digested by BamHI and KpnI which were designed on both ends of the PCR primers. The reverse primer had an artificial restriction enzyme digestion site of BamHI which was aimed at the tail BamHI site of the FPV VP2 gene (FIG. 1). The forward primer carried an artificial restriction enzyme digestion site of KpnI which was aimed at the KpnI site in the gpt fragment of the F3S/FPV plasmid (FIG. 1). The DNA bands were extracted, reseparated on the 1% agarose gel and recovered by a DNA purification kit. The DNA fragments, comprising linearized F3S/FPV and the amplified DNA which had been restricted, were ligated together and the ligation mixture was used to transform *E. coli* DH5α. The transformed *E. coli* cells were plated on the LB agar plate containing 50 µg/ml ampicillin, and incubated at 37° C. overnight. The amp-resistant selected bacterial colonies were screened by colony hybridization using both FPV VP2 and rabies G genes as probes (SEQ ID NO:1 and SEQ ID NO:2, respectively). The colonies positive by hybridization were then selected and cultured in the LB medium for preparation of plasmid DNA. A plasmid, termed F3S/FPV/RAB, was formed which contained rabies-G gene operably linked to a $P_{11}$ and the FPV VP2 gene operably linked to a VV $P_{11}$ promoter (FIG. 1). The purified plasmid DNA was further confirmed by DNA sequencing. Three primers were used to sequence both FPV VP2 and rabies G genes (SEQ ID NOs: 4, 5, and 6). A primer (SEQ ID NO:6) was used to sequence the promoter, the junction of promoter, and VP2 coding sequence. The two PCR primers (SEQ ID NO:4 and SEQ ID NO:5) were used to sequence the inserted PCR fragment. All of the sequenced DNAs were compared with the original published sequences. Note that in F3S/FPV/RAB, the respective exogenous genes, operably linked to their respective promoter, are in opposite orientation (in the direction of transcription) relative to each other. Each inserted gene had its own promoter, start codon and stop codon for authentic protein expression. Thus, both inserted genes were not mutated in this multivalent plasmid.

EXAMPLE 2

Construction of a Recombinant Raccoon Poxvirus

The essential features of a potential viral vaccine vector for use in the immunization of felines according to the present invention include the following features.

(a) The viral vector need be safe and suitable as a vaccine in cats. For example, the viral vector must infect and replicate in cats without causing significant pathology in immunized cats. Also, the viral vector must be capable of expressing genes recombined into it, upon infecting feline cells.

(b) The viral vector must be able to tolerate large foreign insertions (multiple genes inserted by recombination) into either or both of the thymidine kinase gene and the hemagglutinin gene without significantly and negatively affecting the ability of the recombinant virus to infect and replicate in susceptible host cells.

Raccoon poxvirus (RCNV) was found to be safe and suitable as a viral monovalent vaccine vector useful for immunizing cats (Ngichabe, C. K., 1992, supra). However, it was not known at the time of the invention whether raccoon poxvirus could tolerate large foreign insertions, as required when recombining multiple genes/expression cassettes (versus a single gene), into the thymidine kinase gene or its hemagglutinin gene of the raccoon poxvirus genome without the virus losing its ability to infect and replicate in susceptible host cells. Further, it was not known at the time of the invention whether there were any constraints relative to the orientation of insertion of multiple genes with respect to the direction of transcription. Extrapolating the results of studies with VV vectors, relative to the capacity of the viral genome to tolerate insertions and relative to orientation, to RCNV would be presumptuous because the DNA sequences between RCNV and VV are significantly different.

The multivalent RCNV-based recombinant FPV and rabies virus was generated by homologous recombination of the flanked vaccinia virus TK gene sequence connected to both ends of the two insertions (VP2 and rabies-G) with the TK fragment of RCNV. Purified plasmid DNA containing both FPV VP2 and rabies-G genes, with each gene operably linked to a $P_{11}$ promoter, was transfected by calcium phosphate precipitation into CV-1 cell monolayers which were also infected with raccoon poxvirus. When the plaques reached about 60% confluence, the transfection mixture was harvested and freezethawed three times. The recombinant RCNV virus was selected by plaque purification in the presence of 50 μg/ml 5-bromo-2'deoxyuridine (BUDR), and dot blot hybridization using $^{32}$P-labelled FPV VP2 and rabies-G gene probes (SEQ ID NO:1 and SEQ ID NO:2, respectively). The positive plaque was further plaque purified three times in rat-2 TK cells with the presence of BUDR and then grown in CV-1 cells without BUDR. The cells were harvested 1 to 2 days later when maximum CPE was observed. The cell suspension was frozen and thawed three times and sonicated before use as vaccine. If desired, the recombinant RCNV can be pelleted by gradient centrifugation, resuspended, and titrated on Rat-2 cell monolayers, to determine the pfus.

EXAMPLE 3

Molecular Analysis of the Multivalent Recombinant Raccoon Poxvirus

In this embodiment, the multivalent recombinant raccoon poxvirus was analyzed for the presence of the VP2 gene and rabies-G gene. The multivalent recombinant raccoon poxvirus was purified by plaque-purification and selected by dot-blot hybridization using $^{32}$P-labelled VP2 and rabies-G gene probes (SEQ ID NO:1 and SEQ ID NO:2, respectively), as described in Example 2. Further, using DNA isolated from the purified multivalent recombinant raccoon poxvirus, an internal sequence of each of the FPV VP2 and rabies-G genes were enzymatically amplified. Two bands were observed when the enzymatically amplified DNA was run on a 1% agarose gel. The bands were the expected sizes of the rabies-G gene internal sequence, and the FPV VP2 internal sequence. The gel was also probed with both the radiolabelled VP2 and rabies G gene probes after Southern transfer; and the results verify the presence of the VP2 and rabies-G genes in the multivalent recombinant raccoon poxvirus.

EXAMPLE 4

Expression of VP2 and Rabies-G Proteins in the Cells Infected with Multivalent Recombinant Raccoon Poxvirus In this embodiment, the multivalent recombinant raccoon poxvirus was analyzed for expression of the recombined multiple genes.

4.1 Indirect Immunofluorescent Antibody Assay (IFA)

An IFA was performed to detect expression of VP2 and rabies-G by cells infected with the multivalent recombinant raccoon poxvirus. Briefly, the CV-1 or CrFK (Crandell feline kidney) cell monolayers, grown in 8-well chamber slides, were infected with the multivalent recombinant virus at one multiplicity of infection. After fixation in cold acetone for 10 minutes, the cell monolayer was washed in PBS and immersed with 1:10 diluted normal cat serum (from specific-pathogen-free cats; "SPF" cats) for 10 minutes. The slides were then incubated with cat anti-FPV polyclonal antibody diluted 1:200 or mouse anti-rabies-G monoclonal antibody for one hour. The slides were thoroughly washed in PBS and incubated with fluorescein-labelled rabbit anti-mouse antibody for 30 minutes. After washing in PBS, the slides were sealed by glycerol and examined by immunofluorescence microscopy.

Figure 2:
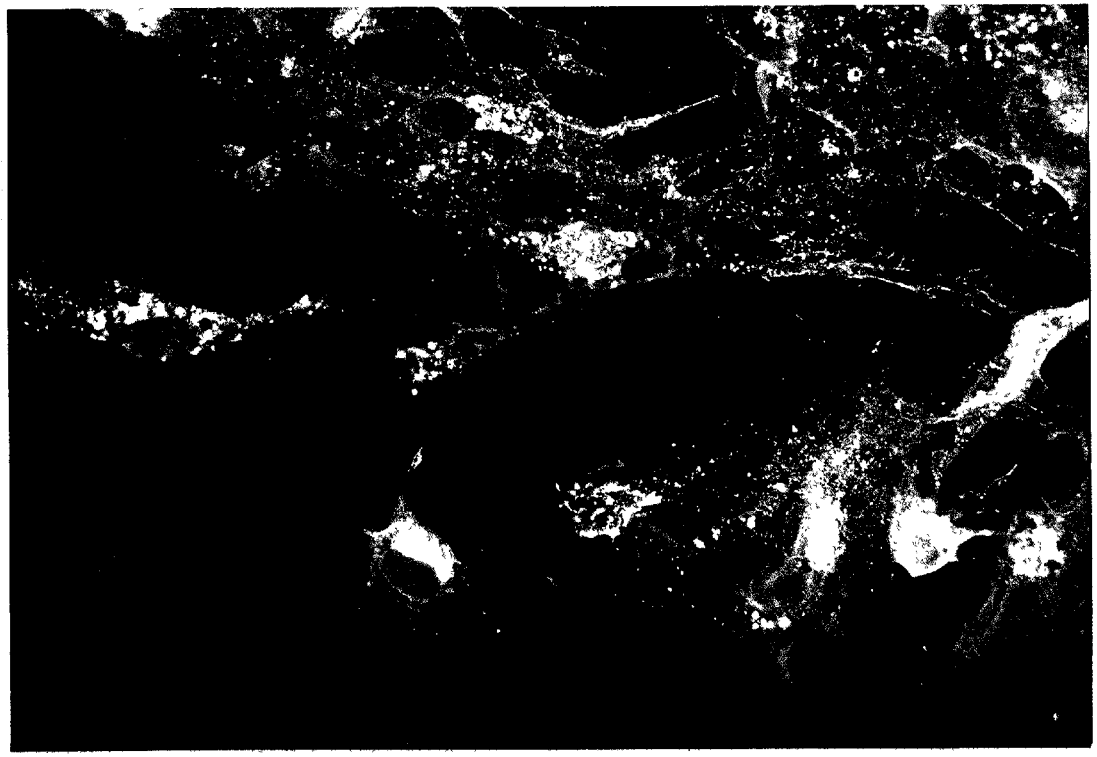
FIG. 2 is a representation (magnification at 250×) showing indirect immunofluorescent assay-positive plaques/cells infected with the multivalent recombinant raccoon poxvirus. Specific fluorescence, indicating expression of VP2, was concentrated in the cytoplasm of infected cells, and was also detected in syncytia cells.
Figure 3:
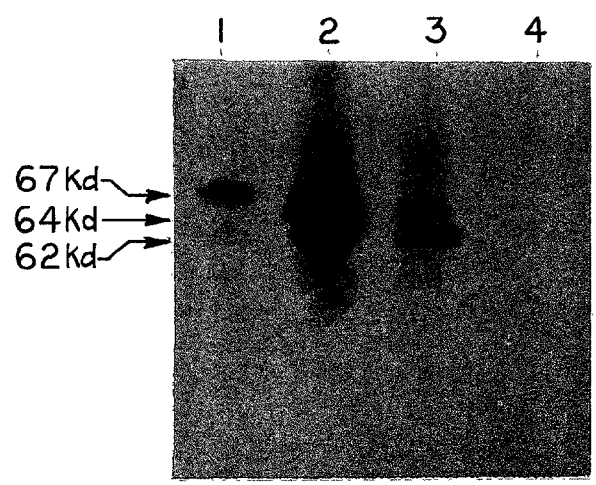
FIG. 3 is a representation of labelled proteins which were precipitated by both cat anti-FPV serum and mouse anti-rabies antibody from $^{35}$S-methionine-labelled RCNV/FPV infected cell lysates, in an immunoprecipitation assay for protein expression.

Immunofluorescence was detected when either cat anti-FPV serum or mouse anti-rabies G monoclonal antibody was reacted with cells infected with multivalent recombinant virus. infected cells or plaques. FIG. 2 shows the IFA-positive plaques/cells infected with the multivalent recombinant raccoon poxvirus. Bright green fluorescence was mostly concentrated on the cytoplasm of the infected cells. Also, IFA detected positive particles in the center of some positive plaques. No difference in strength or patterns of fluorescence was observed when IFA was performed with FPV polyclonal antibody versus with rabies monoclonal antibody.

4.2 Immunoprecipitation Assay

An immunoprecipitation assay was performed to detect expression of VP2 and rabies-G by cells infected with the multivalent recombinant raccoon poxvirus. $^{35}$S-methionine-labelled cell lysate, from CV-1 cells infected with the multivalent recombinant raccoon poxvirus, was immunoprecipitated with cat anti-FPV antiserum and mouse anti-rabies-G monoclonal antibody. Briefly, the CV-1 cell monolayers were infected with the multivalent recombinant raccoon poxvirus, and then were pulse-labelled with $^{35}$S-methionine for 12 hours. The infected cells were lysed in lysis buffer, and all solubilized cellular proteins were separated from the cell debris by centrifugation. The clarified protein suspension was precipitated with anti-FPV antibody or anti-rabies-G monoclonal antibody. The precipitated proteins were loaded onto an 8% to 25% gradient polyacrylamide gel and electrophoresed. The mini-gel was directly fixed, enhanced, and finally neutralized before exposure to X-ray film.

Precipitated proteins, precipitated by both cat anti-FPV serum and mouse anti-rabies antibody from the $^{35}$S-methionine-labelled RCNV/FPV infected cell lysate, are indicated in FIG. 3. The expression of three proteins was observed by the immunoprecipitation assay: FPV VP2 protein of 67 kilodalton (Kd) (FIG. 3, lane 1); and rabies-G1 of 64 Kd, and rabies-G2 of 62 Kd (lane 2). The two rabies bands were very clear if the exposure time was shorter. Lane 4, containing a control cell lysate infected with wild type RCNV, did not show similar bands in the immunoprecipitation assay.

EXAMPLE 5

Vaccine Studies with Multivalent Recombinant Raccoon Poxvirus

In this embodiment, the multivalent recombinant raccoon poxvirus was used to immunize cats to induce an immune response against the feline pathogen antigens expressed by cells infected the multivalent recombinant raccoon poxvirus (RCNV/FPV/RAB-G).

5.1 Preparation of Vaccine Stock

The vaccine stock for the RCNV/FPV/RAB-G construct was prepared using a previously described method for preparing raccoon poxvirus recombinants for use in vaccines (Esposito et al., 1988, *Virology* 165:313–316). CrFK cell monolayers, grown in 150 $cm^2$ tissue culture flasks, were infected with plaque-purified RCNV/FPV/RAB-G at multiple of infectivity=0.5. The multivalent recombinant virus was allowed to adsorb at 37° C. for 2 hours. Supplemented tissue culture medium was added, and the cultures were incubated 24 hours at 37° C. When the confluent CPE was reached, the cells were scraped, concentrated by polyethylene glycol (PEG 8000) and pelleted at 16,000×g for 30 minutes. The pellet was suspended in 1.0 ml of Tris-C1 EDTA (TE), pH 7.6, for every 100 ml of starting culture fluid. Sodium diatrizoate composite gradients were used for layering the suspended mixture. The gradient contained 1 ml of 50% diatrizoate, 25 ml of 25–50% diatrizoate, and 3 ml of Dextran-10. After centrifugation at 125,000×g for 16 hours at 4° C., the viral band was collected, diluted four-fold in TE buffer, and centrifuged through a 30% sucrose cushion. The viral pellet was then resuspended, sonicated, titrated on Rat-2 cells and diluted in 50% v/v in sterile glycerol and TE buffer. The vaccine mixture was finally stored at −20° C. for later use.

5.2 Design of Vaccination and Challenge Studies

The animals used in the vaccination and challenge studies were five- to 6-month-old specific-pathogen-free cats (SPF cat colony) that were kept in regulatory-approved biohazard isolation units. Group A consisted of 9 cats for vaccination. Group B had 2 cats that were unvaccinated controls. Group A was vaccinated subcutaneously three times on days 0, 26, and 34 with recombinant RCNV carrying both FPV VP2 and rabies G genes (RCNV/FPV/RAB-G). Each cat received a dose of $1\times10^7$ PFU virus each time. The control cats received phosphate buffered saline (PBS) at the same time as group A was vaccinated. Sixteen days following the third vaccination, all cats were challenged orally with $10^{4.5}$ $TCID_{50}$ of FPV challenge virus (National Veterinary Service, Ames, Iowa.) strictly following the USDA challenge procedure.

5.3 Vaccination and Challenge Results 5.3.1 Virus Neutralization Antibody Titer

All cats in the vaccination and challenge studies were checked daily for clinical signs. Blood was collected for total white blood cell counts at days 0, 3, 5, 7 and 10 after challenge, and the sera were collected on days 26, 43, 50 and 57 after vaccination. All sera were aliquotted into two vials for both FPV antibody and rabies antibody tests. The viral neutralization antibody assay for antibodies against rabies virus was done by the Rabies Virus Laboratory, New York State Department of Health, Albany, N.Y. The viral neutralization test for rabies virus was done by the rapid immunofluorescent focus inhibition test. The rabies neutralization antibody titers were interpreted as international unit (IU) per ml (1 IU=1:32 virus neutralization titer).

The serum from each cat was also assayed by viral neutralization antibody assays for anti-FPV antibody titer. Briefly, CrFK cells were seeded on 8-chamber slides at $1\times10^3$ cells/ml, and incubated at 37° C. for one hour. Two-fold serial dilutions of all collected serum samples were mixed with an equal volume of 32–100 $TCID_{50}$/0.1 ml of FPV, and were incubated at 37° C. for another hour. The mixtures were then added to individual chambers seeded with CrFK cells and incubated at 37° C. in a 5% $CO_2$ atmosphere for 3 to 4 days. The infected cell monolayers were fixed with methyl alcohol, stained with May Grüwald-Giemsa stain and examined under light microscope for FPV intranuclear inclusions. The highest dilution of serum at which no detectable FPV inclusion bodies were identified was interpreted as the virus neutralization titer.

Figure 4:
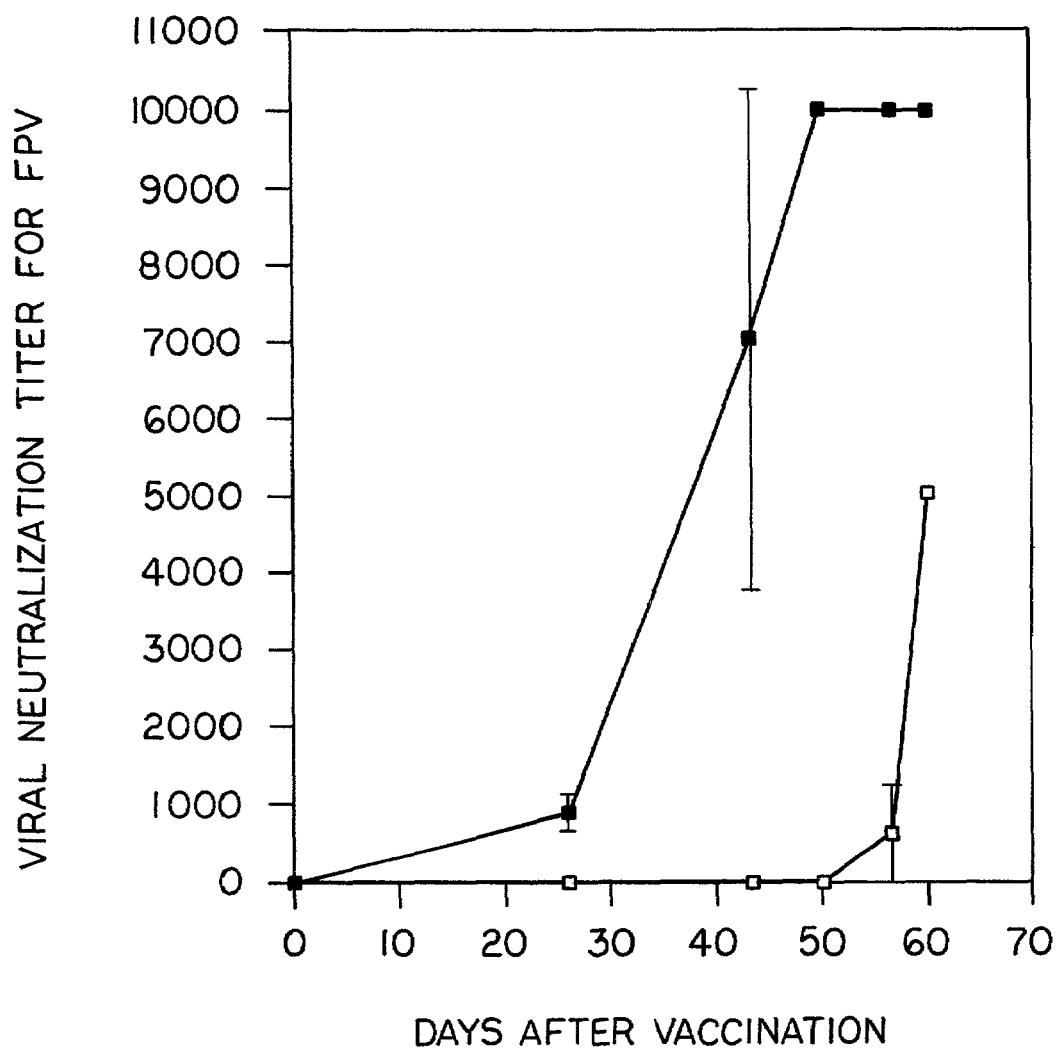
FIG. 4 is a graph showing viral neutralization titers against FPV in cats vaccinated (days 0, 26 and 43) with the multivalent recombinant RCNV vaccine (■), and unvaccinated controls (□) following FPV challenge.

For the FPV virus neutralization assay, the eight cats vaccinated with the multivalent recombinant raccoon poxvirus (RCNV/FPV/RAB-G) achieved a mean virus neutralization titer of 1:1,000 at day 27 (FIG. 4). The virus neutralization titer reached 1:7,000 at day 43, and over 1:10,000 by day 50 (FIG. 4). All three vaccinations boosted the FPV virus neutralization titer, which was not affected by the FPV challenge in vaccinated cats. However, the unvaccinated cats (Group B) obtained virus neutralization titer only after day 50 when the FPV challenge was given. The virus neutralization titer in Group B cats, following challenge with FPV, was as high as 1:5,000 at day 60 (FIG. 4).

For the rabies virus neutralization assay (Table 1), the virus neutralization titer was as high as 4 to 16 international unit (IU) at day 43; and up to 8 to 16 IU at day 50 after vaccination. The virus neutralization titers of two vaccinated cats were ≧8 international units (IU) at day 26; and the titers of 4 vaccinated cats rose to a ≧16 IU by day 43. All of the vaccinated cats obtained a virus neutralization titer over 8 IU at day 50, and four out of 8 vaccinated cats obtained a virus neutralization (VN) titer over 16 IU by day 57 after vaccination. However, the control unvaccinated cats were negative throughout the experiment (Table 1)

TABLE 1

| | Date | RABIES VN TITERS (IU) | | | | |
|---|---|---|---|---|---|---|
| | Cat # | 0 | 26 | 43 | 50 | 57 |
| Unvaccinated cats | A981 | <0.063 | <0.063 | <0.063 | <0.063 | <0.063 |
| | A932 | <0.125 | <0.125 | <0.125 | <0.125 | <0.125 |
| Vaccinated Cats | A983 | <0.063 | 1 | 4 | >=8 | >=8 |
| | A954 | <0.063 | 2 | >=8 | >=8 | >=8 |
| | A962 | <0.063 | 2 | 4 | >=8 | >=8 |
| | A931 | <0.063 | >=8 | >=8 | >=8 | >=8 |
| | A964 | <0.125 | 4 | >=16 | >=16 | >=16 |
| | A982 | <0.125 | 1 | >=16 | >=16 | >=16 |
| | A955 | <0.125 | 1 | >=16 | >=16 | >=16 |
| | A963 | <0.125 | 8 | >=16 | >=16 | >=16 |

(1 IU = 1:32 VN titer)

5.3.2 Leukocyte Counts

Figure 5:
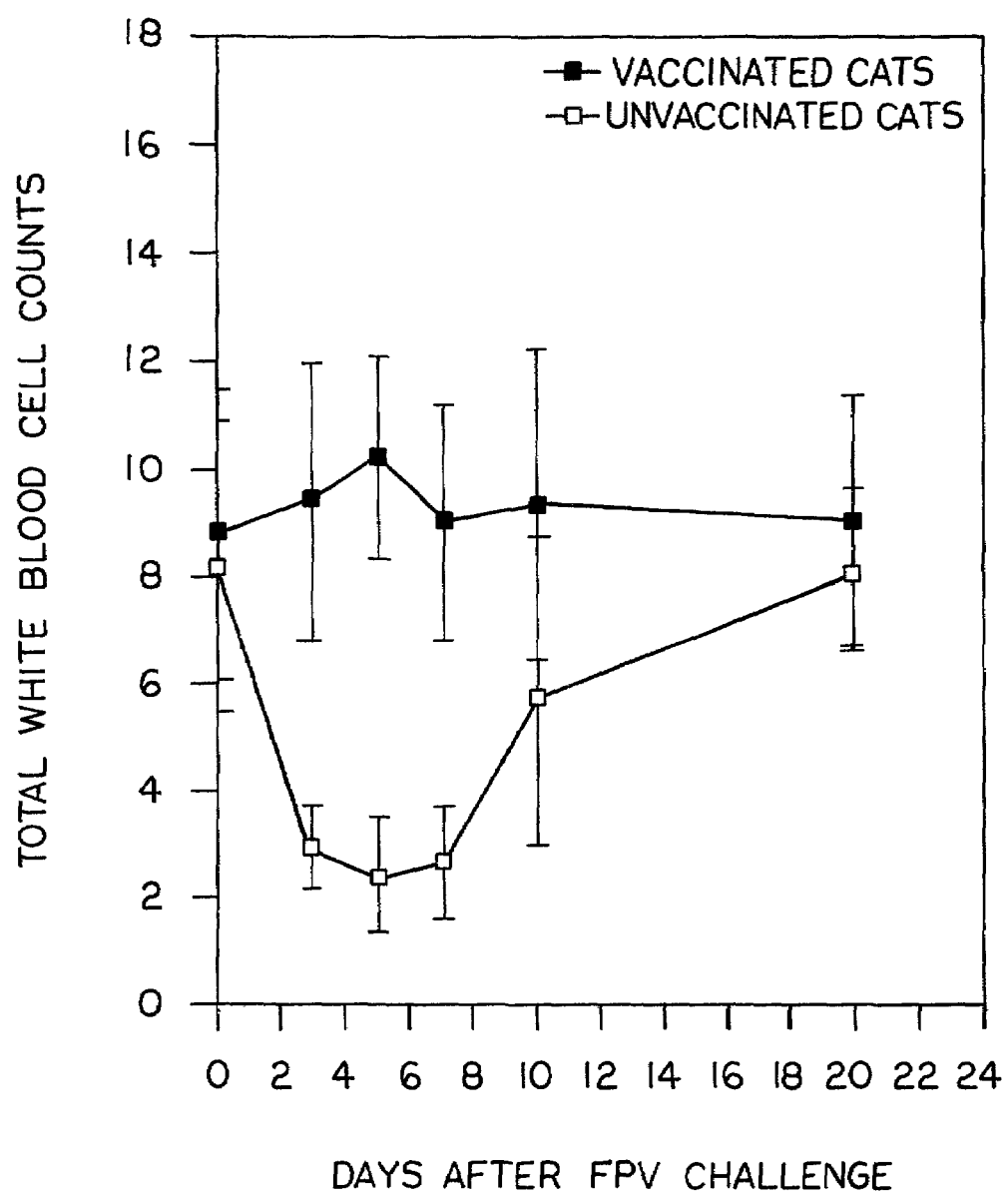
FIG. 5 is a graph showing total white blood cell counts of all vaccinated cats (■) and control cats (□) following FPV challenge.

As described above, blood was collected for total white blood cell counts at days 0, 3, 5, 7 and 10 after challenge. The total white blood cells and differential counts were determined using an automated hematology analyzer. The clinically critical indication of the FPV infection is the change in white blood cell (WBC) counts during the first 10 days after FPV infection. As shown in FIG. 5, total WBC counts of all vaccinated cats were stable in the clinically no=al range throughout the experiment (■). The mean WBC counts of the unvaccinated cats were typical of FPV infection. The mean counts were as low as 2.3 thousand/microliter at day 5 after the FPV challenge (□) and the cats were fully recovered at day 20 when the experiment was ended. This critical indicator of an immune response to FPV demonstrated strong protection of vaccinated cats from subsequent FPV challenge.

Taken together, the vaccination studies indicate that cats vaccinated with the multivalent recombinant raccoon poxvirus were fully protected from FPV challenge, and provoked strong humoral immune responses which may be sufficient to protect the cats from rabies infection. Due to the regulatory restriction of rabies challenge, the efficiency of rabies protection was based on the serum virus neutralization antibody titers following vaccination. However, previous studies have showed that a virus neutralization titer of 0.5 IU is sufficient for protection against rabies virus challenge (Barth et al., 1988, *Vaccine* 6:369–377; Ngichabe, 1992, supra). Thus, the virus neutralization titers of cats vaccinated with the multivalent recombinant raccoon poxvirus vaccine were over 32 fold higher than the recommended satisfactory titers. Based on the data, it is believed cats vaccinated with such a multivalent recombinant raccoon poxvirus would be protected from subsequent rabies virus challenge.

EXAMPLE 6

6.1 Feline Calicivirus as a Feline Pathogen Antigen in a Multivalent Recombinant Raccoon Poxvirus Vaccine Feline calicivirus (FCV) is an important pathogen of cats causing serious feline diseases including acute oral ulceration, mild upper respiratory diseases and severe lower respiratory diseases, and febrile lameness syndrome. In infected cats, FCV is shed in ocular, nasal, and pharyngeal secretions. Cats that have recovered from FCV infection may also become persistent shedders of the virus. The capsid protein of FCV in FCV-infected cells is a 76 Kd protein. Neutralizing epitopes exist on the capsid protein. The nucleotide sequence of the FCV capsid protein was reported recently (Seal et al., 1993, *J. Gen. Virol.* 74:2519–2524; Seal et al., 1995, *Virus Genes* 9:183–187). A cDNA clone of the capsid protein gene (SEQ ID NO:7), from highly virulent strain FCV 255, was used in the construction of a multivalent vaccine as follows.

Using the methods of the present invention, as illustrated in Examples 1–3, an expression cassette can be constructed to include any combination of two or more genes, wherein the genes encode the feline calicivirus (FCV) capsid protein (SEQ ID NO:7), FPV VP2 (SEQ ID NO:1), or rabies-G (SEQ ID NO:2). The expression cassette may then be inserted into an insertion vector, and subsequently recombined into the TK gene of raccoon poxvirus, thereby forming a multivalent recombinant raccoon poxvirus.

Alternatively, genes encoding two or more feline pathogen antigens can be recombined into the hemagglutinin (HA) gene of raccoon poxvirus in forming a multivalent recombinant raccoon poxvirus. In another embodiment, using the methods according to the present invention, both the HA gene and the TK gene can be used as sites into which at least one gene encoding a feline pathogen antigen is recombined into each site (recited in the claims as "a combination thereof"). The vaccinia virus HA gene has been used for construction of vaccinia HA insertion vectors (Shida, 1989, *Subcell. Biochem.* 15:405–440; Shida et al., 1983, *Cell* 33:423–434). The HA sequence is not essential for virus reproduction or infectivity in cell culture, but it affects the way that the virus is disseminated. The HA glycoprotein, synthesized by rough endoplasmic reticulum in the plasma membrane, gives both hemagglutination and hemadsorption. Thus, using hemagglutination and hemadsorption assays, mutations of the HA gene allow screening and selection of the HA phenotype.

Analysis of the HA genes of both RCNV and vaccinia virus showed homology of 69% in DNA sequences and 53% in amino acids of the HA between RCNV and VV (Cavallaro et al., 1992, *Virology* 190:434–439). Thus, the low HA homology between the two viruses excludes the possibility of, and would teach against one skilled in the art to attempt, using vaccinia HA insertion vectors for homologous recombination into the RCNV HA gene.

6.2 Construction of a Recombinant HA Insertion Plasmid

The essential features of an HA insertion plasmid that is useful in the method of the present invention include the following features.

(a) The plasmid sequences flanking the insertion site into which are to be inserted multiple genes, contain sequences which have sufficient homology with sequences present in the raccoon poxvirus genome to mediate recombination. Thus, to construct such a HA insertion vector, raccoon poxvirus HA sequence was used as the flanking sequences to position a vaccinia virus promoter and the insert containing one or more genes that is expected to be expressed. Although the HA flanking sequences can be synthesized to vary slightly from the HA sequence found in RCNV, there must be a sufficient degree of identity ("homology") to promote hybridization of the HA flanking sequence to the HA gene sequence of raccoon poxvirus and subsequent recombination. Alternatively, such flanking sequences can be part of the insert to be inserted into the plasmid.

(b) The flanking sequences must be homologous to a region of the raccoon poxvirus (into which the multiple genes are recombined) that is nonessential for the growth and propagation of the raccoon poxvirus. As illustrated in this Example, the hemagglutinin (HA) gene of the raccoon poxvirus genome can be used for insertion of exogenous genes by recombination. Insertion of exogenous genes into the HA gene by recombination results in recombinant raccoon poxvirus capable of infection and replication, and can be used for expression of the recombined exogenous genes in host cells infected with the recombinant virus.

Desirable features of an insertion plasmid that is useful in the method of the present invention include the following features.

(a) Although it is possible that exogenous genes recombined into the raccoon poxvirus genome may be expressed without first operably linking the genes with one or more control element elements for expression (such as a promoter) prior to recombination, operably linking the control element(s) to the multiple genes (thereby forming an expression cassette) before using the genes for insertion into the plasmid insertion vector, will likely result in higher efficiency of expression of the recombined genes. Alternatively, the sequences flanking the insertion site of the plasmid insertion vector can be engineered to contain the control elements which are then operably linked to the multiple genes upon insertion.

(b) Although one promoter may be used to drive the expression of two exogenous genes to be recombined, use of two promoters in an insertion vector, each promoter operably linked to an individual exogenous gene, will provide higher efficiency of expression.

Thus, in this embodiment, RCNV HA sequence was used as flanking sequences to position a promoter operably linked to the foreign gene insert that is to be expressed. To illustrate this embodiment, a 2381 bps cDNA fragment amplified from the pSV.SPORT1/FCV cDNA clone (FIG. 5) was flanked with an XhoI site at the 5'-start codon end and KpnI at the 3' end. A vaccinia TK insertion plasmid, pMJ601, was digested with SalI and KpnI. The FCV fragment, containing the capsid protein gene, was ligated into pMJ601 to form a plasmid, termed pMJ601/FCV. By such insertion, the FCV capsid protein gene was operably linked to a vaccinia late promoter. The plasmid DNA was sequenced to confirm the accuracy of the cloned fragment, and the open reading frame orientation.

Figure 6A:
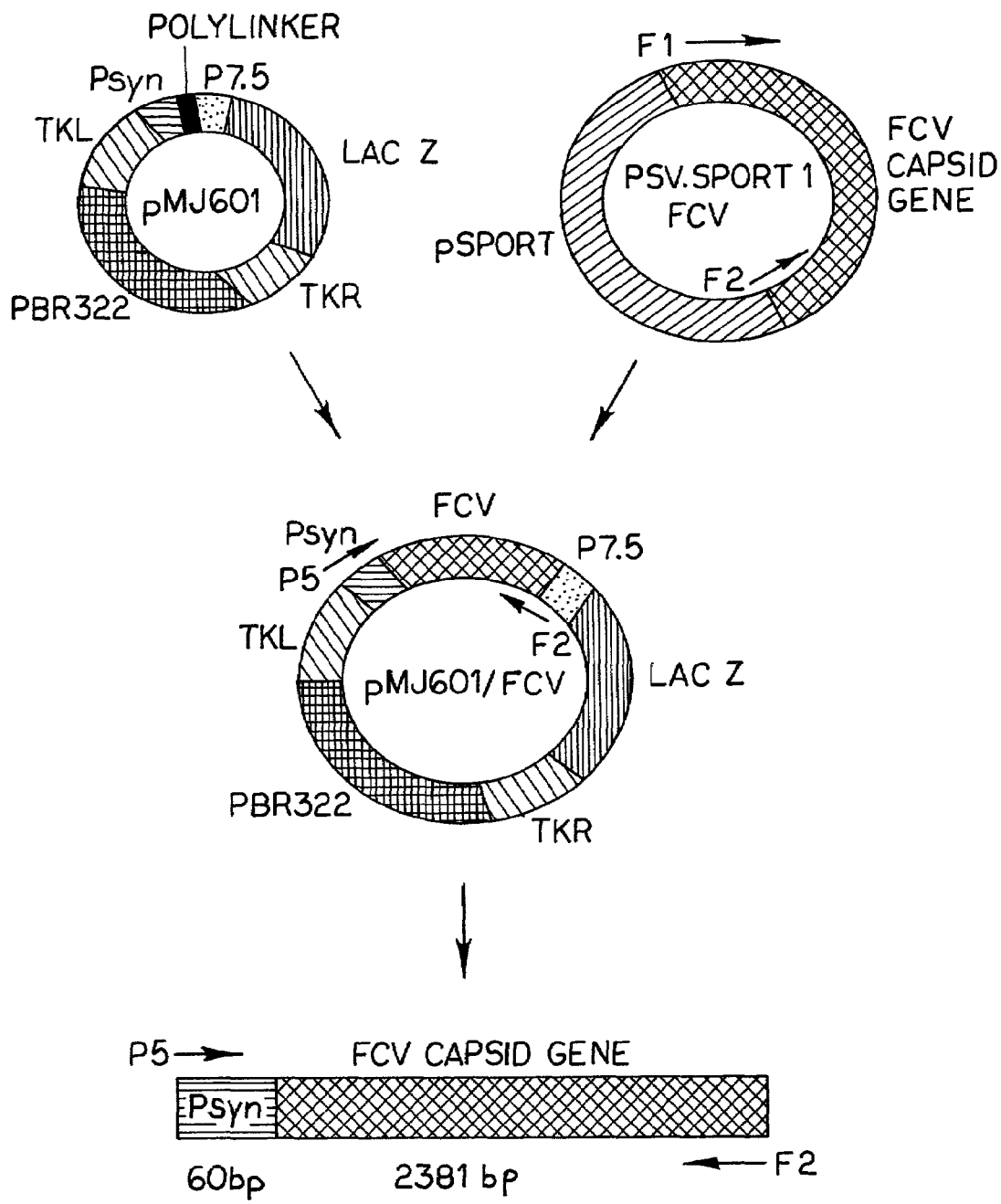
FIG. 6A is a schematic showing enzymatic amplification of the FCV capsid protein gene, and subcloning the amplified FCV fragment into a vaccinia insertion vector.
Figure 6B:
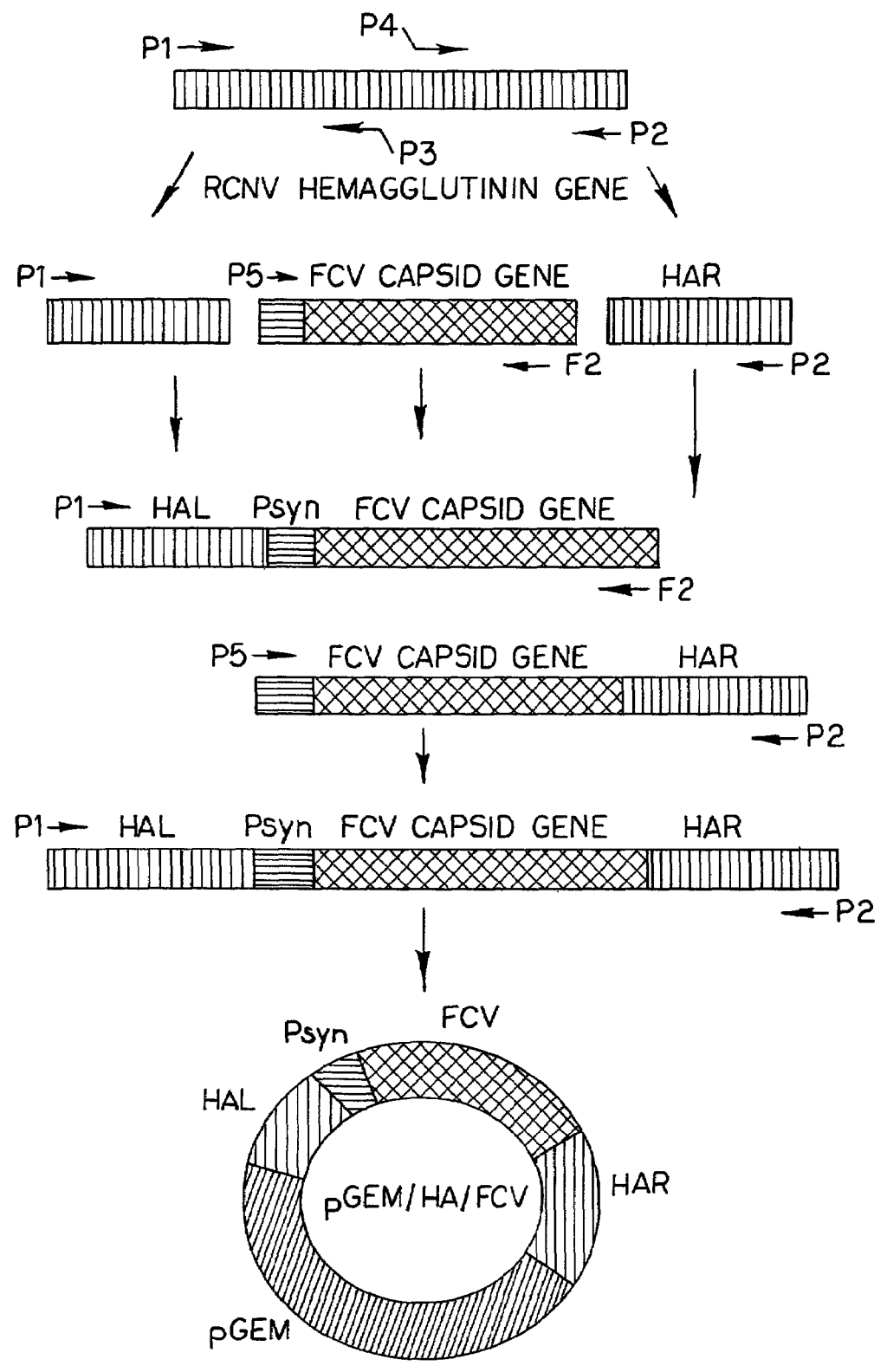

A RCNV HA fragment of 1,262 base pairs (bp) was divided into two parts from which a HA left arm (HAL) and a right arm (HAR) were prepared by enzymatic amplification using the polymerase chain reaction (PCR). The HA left arm of 582 bps (SEQ ID NO:8) and the HAR of 447 bps (SEQ ID NO:9) were amplified using primers P1, P2, P3 and P4 (FIG. 6). The middle portion of the HA gene (between HAL and HAR) was deleted after forming the two end fragments. The amplified products of HAL, HAR, and of the capsid protein gene operably linked to a promoter (P/FCVCP), were joined and amplified by recombinant PCR. The full sequence, which contained HAL-P/FCVCP-HAR of 3,353 bp was prepared from two recombinant fragments. Conditions typically used for enzymatic amplification, include a denaturation step at 95° C. for 1 minute, an annealing step at 60° C. for 1 minute, an extension at 72° C. for 3 minutes, an extra extension at 72° C. for 7 minutes, and a soaking step at 4° C. for analysis. For FCV capsid protein gene amplification, an annealing temperature at 68° C. was applied and other temperatures were the same as above. Enzymatically amplified fragments of HAL and P/FCVCP were joined by recombinant PCR using the 20 bps overhang sequence of a primer, P3 (SEQ ID NO:10). About 10 to 50 ng of purified DNA fragments of HAL and P/FCVCP were mixed with a thermostable DNA polymerase without primers. The first three cycles of PCR were designed for ligation of the two fragments in the presence of the thermostable DNA polymerase. The protocol of the thermocycle steps was as follows: denature at 94° C. for 1 minute, anneal at 40° C. for 2 minutes at a ramp rate of 6 seconds/per degree and extension at 72° C. for 3 minutes at ramp rate of 2 seconds/per degree. Primers P1 (SEQ ID NO:11) and F2 (SEQ ID NO:12) were added to the reaction tube and a regular PCR was performed for 30 cycles with denaturation at 94° C. for 1 minute, annealing at 55° C. for 1 minute and extension at 72° C. for 2 minutes (See also, FIG. 6A). A final incubation at 72° C. for 7 minutes was used for the extension of all amplified fragments. Using the same protocol and conditions, amplified fragments of P/FCVCP and HAR were ligated by primers P5 (SEQ ID NO:13) and P2 (SEQ ID NO:14) (See also, FIG. 6B). All of the amplified products were purified from 1% agarose gel by a DNA purification kit.

The low annealing temperature (40° C.) and ramp temperature during the turnover of each thermocycle step greatly facilitated the process of recombination. After two to three cycles without primer, the ligated fragment was amplified by PCR. The resultant recombinant product, HAL-P/FCVCP-HAR, was ultimately subcloned into plasmid pGEM-3Z to form a novel RCNV HA insertion plasmid carrying FCV, termed pGEM/FCV. The total length of the plasmid was 6175 bps which included 3353 bps of HAL-P/FCVCP-HAR and 2726 bps of pGEM (FIG. 6B).

6.3 Construction of a Recombinant Raccoon Poxvirus

Homologous recombination between the RCNV HA sequences of pGEM/FCV and between the HA sequences of wild type RCNV was performed with procedures outlined in Example 2, and as described previously (See for example, Mackett et al., *J. Virol.* 49:857–864, herein incorporated by reference). Briefly, the purified HA insertion vector, pGEM/FCV, was precipitated onto a CV-1 cell monolayer infected with wild type RCNV by calcium phosphate transfection. After 48 hours of the transfection, the cell monolayer was frozen and thawed three times. The virus mixture was plated at different dilutions onto the CV-1 monolayer and grown in the 8-well chamber slide. When CPE appeared, the cells were fixed and stained with cat anti-FCV serum.

Figure 7A:
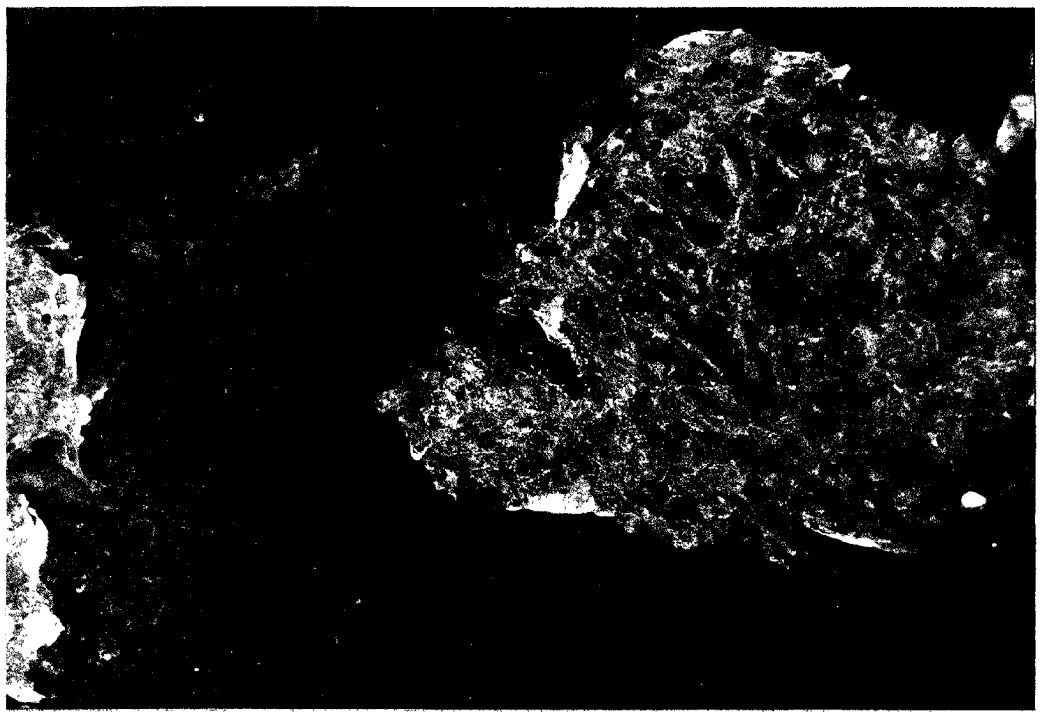
FIG. 7A shows positive plaques in a heavily infected well at lower magnification (50×).
Figure 7B:
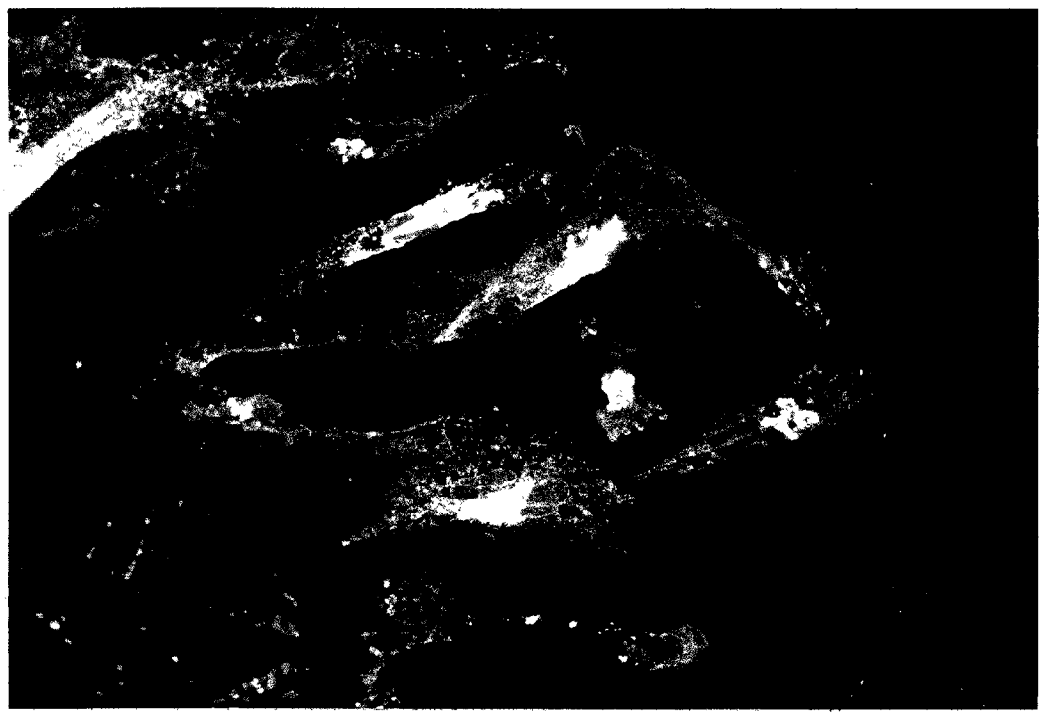
FIG. 7B shows positive plaques at higher magnification (50 OX).

6.4 Expression of FCV Capsid Protein in Cells Infected with a Recombinant Raccoon Poxvirus Indirect immunofluorescent antibody assays were performed to detect FCV-specific fluorescence in the cytoplasm and plasma membrane in infected cells and recombinant raccoon poxvirus-formed plaques in cell culture. CV-1 cell monolayers were infected with the recombinant RCNV or wild type RCNV and incubated for 18 to 24 hours at 37° C. The infected cell monolayers were fixed in cold acetone, incubated first with 1:10 diluted normal cat serum for 10 minutes, and then with 1:100 diluted cat anti-FCV antiserum for one hour at room temperature. The monolayer was finally stained in 1:100 diluted fluorescein labelled rabbit anti-cat IgG for 30 minutes and examined by fluorescent microscopy. The immunofluorescent antibody assay showed that positive viral plaque and/or positive infected cells were detectable by specific FCV antibody. FIG. 7A shows two separate positive plaques in a heavily infected well at lower magnification. FIG. 7B shows recombinant virus-induced plaques at higher magnification. The cytoplasm of the infected cells and the syncytia cells were heavily stained with intensive fluorescence. Even though the fluorescent particles were more likely concentrated around the nucleus, the positive particles were distributed all over the cytoplasm and plasma membrane. All of the wild type RCNV-infected cells were negative.

6.4 Vaccines Comprising Recombinant Raccoon Poxvirus Containing FCV Capsid Protein Gene Using the methods according to Example 5, vaccine stocks of recombinant raccoon poxvirus containing FCV capsid protein gene can be prepared, and administered in a vaccination process to felines.

EXAMPLE 7

Alternatives in Feline Pathogen Antigen Expression

The selection of a promoter may depend on the feline pathogen antigen to be expressed. Promoters vary in strength, i.e. ability to facilitate transcription. Generally, for the purpose of expressing a cloned gene, it is desirable to use a strong promoter in order to obtain a high level of transcription of the gene and expression into gene product. For example, viral promoters known in the art, which may be used in a multivalent recombinant raccoon poxvirus, from which a high level of transcription has been observed in infected mammalian cells include the SV40 early promoter, CMV promoters, various vaccinia promoters, adenovirus major late promoter, and the like, may be used to provide transcription of the inserted DNA sequence encoding feline pathogen antigens.

To improve the efficiency of expression of feline pathogen antigens, it is preferable that each gene encoding an antigen is operably linked to a promoter. However, for some promoters, such as the vaccinia virus $P_{11}$ promoter, apparently two genes with the same kind of promoter can not be oriented in the same direction in the recombinant raccoon poxvirus. Thus, a gene to be expressed may have to be inserted in a transcription orientation which is opposite to the transcription orientation of an adjacent gene to be expressed.

Other control elements for efficient gene transcription or message translation include enhancers, and regulatory signals. Enhancer sequences are DNA elements that appear to increase transcriptional efficiency in a manner relatively independent of their position and orientation with respect to a nearby gene. Thus, an enhancer may be placed either upstream or downstream from the inserted DNA sequences encoding feline pathogen antigens to increase transcriptional efficiency.

Further, genetic engineering techniques can be used to reduce a gene to a gene fragment that encodes only a portion of the feline pathogen antigen; but a portion that acts as an immune response-inducing epitope. For example, from the sequences of the various genes feline pathogen, it can be determined which restriction enzyme or combination of restriction enzymes may be used to generate sequences encoding immunogenic peptides. Restriction enzyme selection may be done so as not to destroy the immunopotency of the resultant peptide. Antigenic sites of a protein may vary in size but can consist of from about 7 to about 14 amino acids. Thus, a protein the size of most feline pathogen antigens may contain many discrete antigenic sites; therefore, many partial gene sequences could encode antigenic epitopes. Consequently, using the nucleotide sequence of the particular gene as a guide, restriction enzyme combinations may be used to generate DNA sequences, which when inserted into a multivalent recombinant raccoon poxvirus, are capable of directing the production of peptides comprising one or more antigenic epitopes.

Modification of the feline pathogen antigens or peptides, such as by deletion and substitution of amino acids (and including extensions and additions to amino acids) and in other ways, may be made so as to not substantially detract from the immunological properties of the antigen or peptide. In particular, the amino acid sequence of the antigen or peptide, may be altered by replacing one or more amino acids with functionally equivalent amino acids resulting in an alteration which is silent in terms of an observed difference in the physicochemical behavior of the antigen or peptide. Functionally equivalent amino acids are known in the art as amino acids which are related and/or have similar polarity or charge. Thus, an amino acid sequence which is substantially that of the amino acid sequences depicted in the Sequence Listing herein, refers to an amino acid sequence that contains substitutions with functionally equivalent amino acids without changing the primary biological function of antigen, or peptide.

Also, it will be appreciated by those skilled in the art, that because of third base degeneracy, almost every amino acid is represented by more than one triplet codon in a coding nucleotide sequence. Thus, a gene encoding a feline pathogen antigen as disclosed herein, may be modified slightly in nucleotide sequence, and yet still encode its respective gene product of the same amino acid sequence. Thus, insertion of such modified genes into a multivalent recombinant raccoon poxvirus is within the scope of the present invention.

EXAMPLE 8

Feline Infectious Peritonitis Virus as a Feline Pathogen Antigen in a Multivalent Recombinant Raccoon Poxvirus Vaccine Feline infectious peritonitis virus (FIPV) is a coronavirus which causes a highly fatal disease in infected cats. It has been shown that in coronavirus infections, antibodies may be developed against the membrane glycoprotein (M) and the nucleocapsid protein (N) which can inhibit virus replication. The nucleotide sequences of the FIPV M (SEQ ID NO:17) and N (SEQ ID NO:18) genes, and their deduced amino acid sequences, have been described previously (Vennema et al., 1991, *Virology* 181:327–335; the disclosure of which is herein incorporated by reference).

Using the methods of the present invention, as illustrated in Examples 1–3, and 7, an expression cassette can be constructed to include any combination of two or more genes, wherein one of the genes encodes either the FIPV M or N protein. Other exogenous genes that can be included in such an expression cassette include genes that encode FCV capsid protein, FPV VP2, or rabies-G. The expression cassette may then be inserted into an insertion vector, and subsequently recombined into the TK gene of raccoon poxvirus, thereby forming a multivalent recombinant raccoon poxvirus.

Alternatively, using the methods of the present invention, as illustrated in Examples 1–4, 6, and 7, an expression cassette can be constructed to include any combination of two or more genes, wherein one of the genes encodes either the FIPV M or N protein. Other exogenous genes that can be included in such an expression cassette include genes that encode the FCV capsid protein, FPV VP2, or rabies-G. The expression cassette may then be inserted into an insertion vector, and subsequently recombined into the HA gene of raccoon poxvirus, thereby forming a multivalent recombinant raccoon poxvirus.

In another embodiment, using the methods according to the present invention, both the HA gene and the TK gene can be used as sites into which exogenous genes encoding feline pathogen antigens are recombined into raccoon poxvirus. Combinations of such exogenous genes include genes which encode FIPV M, FIPV N, FCV capsid protein, FPV VP2, and rabies-G. With all of these embodiments, using the methods according to Example 5 and other methods known in the art, vaccine stocks of recombinant raccoon poxvirus containing exogenous genes encoding feline pathogen antigens can be prepared, and administered in a vaccination process to felines.

EXAMPLE 9

Feline Immunodeficiency Virus as a Feline Pathogen Antigen in a Multivalent Recombinant Raccoon Poxvirus Vaccine Feline immunodeficiency virus (FIV) is a retrovirus which causes a persistent generalized lymphadenopathy, recurrent fevers, anorexia, and weight loss in infected cats. Often chronic secondary infections are present which are caused by other feline pathogens. A comprehensive review of FIV biology, infection, and immune responses thereto, has been recently published (Bendinelli et al., 1995, *Clin. Microbiol. Reviews* 8:87–112; the disclosure of which is hereby incorporated by reference). In vaccine studies, cats receiving immunizations with either inactivated whole-infected cell or cell-free feline immunodeficiency virus (FIV) vaccines were protected against subsequent FIV challenge; wherein protection appeared to correlate with antiviral envelope antibody titers (Yamamoto et al., 1993, *J. Virol.* 67:601–605). The gene encoding FIV Gag protein (approximately FIV nucleotide sequence base 600 to base 2,000; Bendinelli et al., supra), or the gene the FIV Env protein (approximately FIV nucleotide sequence base 6,250 to base 8,850; Bendinelli et al., supra) may be used to induce neutralizing antibodies which may inhibit virus infection and/or replication.

Using the methods of the present invention, as illustrated in Examples 1–4, and 7, an expression cassette can be constructed to include any combination of two or more genes, wherein one of the genes encodes either the FIV Gag or Env protein. Other exogenous genes that can be included in such an expression cassette include genes that encode FIPV M, FIPV N, FCV capsid protein, FPV VP2, or rabies-G. The expression cassette may then be inserted into an insertion vector, and subsequently recombined into the TK gene of raccoon poxvirus, thereby forming a multivalent recombinant raccoon poxvirus.

Alternatively, using the methods of the present invention, as illustrated in Examples 1–4, 6, and 7, an expression cassette can be constructed to include any combination of two or more genes, wherein one of the genes encodes either FIV Gag or FIV Env. Other exogenous genes that can be included in such an expression cassette include genes that encode FIPV M, FIPV N, FCV capsid protein, FPV VP2, or rabies-G. The expression cassette may then be inserted into an insertion vector, and subsequently recombined into the HA gene of raccoon poxvirus, thereby forming a multivalent recombinant raccoon poxvirus.

In another embodiment, using the methods according to the present invention, both the HA gene and the TK gene can be used as sites into which exogenous genes encoding feline pathogen antigens are recombined into raccoon poxvirus. Combinations of such exogenous genes include genes which encode FIV Gag, FIV Env, FIPV M, FIPV N, FCV capsid protein, FPV VP2, and rabies-G. With all of these embodiments, using the methods according to Example 5 and other methods known in the art, vaccine stocks of recombinant raccoon poxvirus containing exogenous genes encoding feline pathogen antigens can be prepared, and administered in a vaccination process to felines.

EXAMPLE 10

Feline Leukemia Virus as a Feline Pathogen Antigen in a Multivalent Recombinant Raccoon Poxvirus Vaccine Feline leukemia virus (FeLV) is a oncornavirus which causes leukemia and related symptoms in infected cats. FeLV env gene expression via a canarypox virus-based vector, was used as the basis for a vaccine in cats (Tartaglia et al., 1993, *J. Virol.*67:2370–2375). The nucleotide sequence of the FeLV env gene (SEQ ID NO:19), the deduced amino acid sequence of its gene product Env, and neutralizing regions of Env have been disclosed previously (Stewart et al., 1986, *J. Virol.* 58:825–834; Elder et al., 1987, *J. Virol.* 61:8–15, respectively; the disclosures of which are herein incorporated by reference). Cats immunized with the vaccine resisted subsequent challenge with FeLV, in the absence of detectable FeLV-neutralizing antibodies.

Using the methods of the present invention, as illustrated in Examples 1–4, and 7, an expression cassette can be constructed to include any combination of two or more genes, wherein one of the genes encodes the FeLV Env protein. Other exogenous genes that can be included in such an expression cassette include genes that encode FIV Gag, FIV Env, FIPV M, FIPV N, FCV capsid protein, FPV VP2, or rabies-G. The expression cassette may then be inserted into an insertion vector, and subsequently recombined into the TK gene of raccoon poxvirus, thereby forming a multivalent recombinant raccoon poxvirus.

Alternatively, using the methods of the present invention, as illustrated in Examples 1–4, 6, and 7, an expression cassette can be constructed to include any combination of two or more genes, wherein one of the genes encodes FELV Env. Other exogenous genes that can be included in such an expression cassette include genes that encode FIV Gag, FIV Env, FIPV M, FIPV N, FCV capsid protein, FPV VP2, or rabies-G. The expression cassette may then be inserted into an insertion vector, and subsequently recombined into the HA gene of raccoon poxvirus, thereby forming a multivalent recombinant raccoon poxvirus.

In another embodiment, using the methods according to the present invention, both the HA gene and the TK gene can be used as sites into which exogenous genes encoding feline pathogen antigens are recombined into raccoon poxvirus. Combinations of such exogenous genes include genes which encode FeLV Env, FIV Gag, FIV Env, FIPV M, FIPV N, FCV capsid protein, FPV VP2, and rabies-G. With all of these embodiments, using the methods according to Example 5 and other methods known in the art, vaccine stocks of recombinant raccoon poxvirus containing exogenous genes encoding feline pathogen antigens can be prepared, and administered in a vaccination process to felines.

It should be understood that while the invention has been described in detail herein, the examples were for illustrative purposes only. Other modifications of the embodiments of the present invention that are obvious to those skilled in the art of molecular biology, veterinary medicine, and related disciplines are intended to be within the scope of the appended claims.

What is claimed is:

1. A multivalent recombinant raccoon poxvirus which can infect and replicate in feline cells, and contains more than one exogenous gene inserted into a region consisting of a thymidine kinase gene of the raccoon poxvirus genome which is non-essential for viral replication, wherein:
   (a) the exogenous genes are operably linked to a promoter for expression; and
   (b) each exogenous gene encodes a feline pathogen antigen.

2. The multivalent recombinant raccoon poxvirus according to claim 1, wherein the exogenous genes encode feline pathogen antigens selected from the group consisting of FELV Env, FIV Gag, FIV Env, FIPV M, FIPV N, FCV capsid protein, FPV VP2, and rabies-G.

3. The multivalent recombinant raccoon poxvirus according to claim 1, wherein the exogenous genes are inserted as an expression cassette.

4. The multivalent recombinant raccoon poxvirus according to claim 1, wherein the recombinant raccoon poxvirus was produced by a recombination process comprising the steps of:
   (a) inserting more than one exogenous gene into an insertion vector which has sequences, flanking the inserted genes, having sufficient homology to a region of the raccoon poxvirus genome to promote recombination of the inserted genes into the thymidine kinase gene;
   (b) introducing both the insertion vector containing the exogenous genes, and raccoon poxvirus into susceptible host cells; and
   (c) selecting the recombinant raccoon poxvirus, containing the exogenous genes which have recombined into the raccoon poxvirus genome, from plaques resulting from step (b).

5. The multivalent recombinant raccoon poxvirus according to claim 4, wherein the exogenous genes are inserted as an expression cassette.

6. A method of vaccinating a feline against feline pathogens, said method comprises administering to the feline a prophylactically effective amount of a multivalent recombinant raccoon poxvirus which can infect and replicate in feline cells, and contains more than one exogenous gene inserted into a region consisting of a thymidine kinase gene of the raccoon poxvirus genome which is non-essential for viral replication, wherein:
   (a) the exogenous genes are operably linked to a promoter for expression; and
   (b) each exogenous gene encodes a feline pathogen antigen.

7. The method of claim 6, wherein the exogenous genes encode feline pathogen antigens selected from the group consisting of FELV Env, FIV Gag, FIV Env, FIPV M, FIPV N, FCV capsid protein, FPV VP2, and rabies-G.

8. The method of claim 6, wherein the exogenous genes are inserted as an expression cassette.

9. The method of claim 6, wherein the recombinant raccoon poxvirus was produced by a recombination process comprising the steps of:
   (a) inserting more than one exogenous gene into an insertion vector which has sequences, flanking the inserted genes, having sufficient homology to a region of the raccoon poxvirus genome to promote recombination of the inserted genes into the thymidine kinase gene;
   (b) introducing both the insertion vector containing the exogenous genes, and raccoon poxvirus into susceptible host cells; and
   (c) selecting the recombinant raccoon poxvirus, containing the exogenous genes which have recombined into the raccoon poxvirus genome, from plaques resulting from step (b).

10. The method of claim 9, wherein the exogenous genes are inserted as an expression cassette.

* * * * *